US012157125B2

(12) United States Patent
Anderson

(10) Patent No.: US 12,157,125 B2
(45) Date of Patent: Dec. 3, 2024

(54) MICROPLATE HOLDER FOR IMAGING SYSTEM

(71) Applicant: ARACELI BIOSCIENCES INC., Tigard, OR (US)

(72) Inventor: Marshall Anderson, Portland, OR (US)

(73) Assignee: ARACELI BIOSCIENCES, INC., Tigard, OR (US)

( * ) Notice: Subject to any disclaimer, the term of this patent is extended or adjusted under 35 U.S.C. 154(b) by 523 days.

(21) Appl. No.: 17/445,383

(22) Filed: Aug. 18, 2021

(65) Prior Publication Data
US 2023/0057099 A1 Feb. 23, 2023

(51) Int. Cl.
*B01L 3/00* (2006.01)
*C12M 1/32* (2006.01)
*G01N 21/64* (2006.01)

(52) U.S. Cl.
CPC ............ *B01L 3/5085* (2013.01); *C12M 23/12* (2013.01); *G01N 21/6452* (2013.01); *B01L 2300/0829* (2013.01)

(58) Field of Classification Search
CPC .......... B01L 3/5085; B01L 2300/0829; C12M 23/12; G01N 21/6452
See application file for complete search history.

(56) References Cited

U.S. PATENT DOCUMENTS

| | | | | |
|---|---|---|---|---|
| 4,881,863 | A | * | 11/1989 | Braginsky ............ G01R 31/308 414/935 |
| 7,700,903 | B2 | | 4/2010 | Weiss et al. |
| 9,772,540 | B2 | | 9/2017 | Norris et al. |
| 2009/0195866 | A1 | | 8/2009 | Kawaski et al. |
| 2016/0123886 | A1 | | 5/2016 | Jaffe et al. |
| 2016/0187636 | A1 | | 6/2016 | Ingber et al. |

FOREIGN PATENT DOCUMENTS

| | | |
|---|---|---|
| CN | 102589463 B | 1/2014 |
| JP | H08125891 A | 5/1996 |

OTHER PUBLICATIONS

ISA Korean Intellectual Property Office, International Search Report and Written Opinion Issued in Application No. PCT/US2022/075080, Dec. 1, 2022, WIPO, 12 pages.
"The Nikon Perfect Focus System (PFS)," Microscopy U Website, Available Online at https://www.microscopyu.com/tutorials/the-nikon-perfect-focus-system-pfs, Available as Early as Aug. 1, 2016, 3 pages.
Policelli, M. et al., "High Throughput Microscope Assembly," U.S. Appl. No. 17/445,381, filed Aug. 18, 2021, 99 pages.
Policelli, M. et al., "High Throughput Quantitative Microscopy System," U.S. Appl. No. 17/445,388, filed Aug. 18, 2021, 98 pages.
Policelli, M. et al., "Method and Systems for Autofocusing," U.S. Appl. No. 17/445,396, filed Aug. 18, 2021, 98 pages.
Policelli, M. et al., "Light Synchronization for an Imaging System," U.S. Appl. No. 17/445,387, filed Aug. 18, 2021, 99 pages.

* cited by examiner

*Primary Examiner* — Jamil Ahmed
(74) *Attorney, Agent, or Firm* — McCoy Russell LLP

(57) ABSTRACT

Methods and systems are provided for a sample holder for a multi-detector quantitative microscopy system. In one example, the sample holder includes a frame with a central opening, a pivotable arm positioned adjacent to the central opening and having a whippletree assembly at a first end of the pivotable arm, and a movable ram, in contact with a second end of the pivotable arm, the movable ram configured to pivot the pivotable arm.

14 Claims, 27 Drawing Sheets

FIG. 11A

MICROPLATE HOLDER FOR IMAGING SYSTEM

FIELD

The present description relates generally to methods and systems for high throughput quantitative microscopy.

BACKGROUND/SUMMARY

Application of microscopy to high throughput screening has become a powerful and efficient method for drug development, as well as other biological and chemical experimentation. As such, microscopy may be used to extract quantitative data from images, in contrast to early applications when microscopy only allowed for qualitative analysis. In particular, when quantitative microscopy is paired with sample screening using microplates (e.g., microtiter plates), multiple samples may be analyzed concurrently, thereby expediting sampling throughput.

With current efforts to develop cutting-edge treatments to existing and newly-discovered conditions, medical, biological, and chemical advances may be hindered by a rate at which samples can be screened. More rapid processing and analysis of samples enables examination of more compounds and/or conditions, expediting discovery of new results and findings. Furthermore, faster screening may allow time-dependent biological processes to be observed, thereby providing more useful and relevant information. In particular, application of accelerated screening to studying live cells may enable generation of high quality, accurate models for drug discovery.

For example, a microscopic system configured to provide high throughput data may process samples at a speed dependent on a field-of-view of the microscope objective at a desired magnification and resolution. Each image collected by the system may capture only a small region of a well of a microplate, thereby demanding numerous imaging cycles before screening of the microplate is complete. However, observation of rare biological events and findings, upon which advances in drug treatment may depend, may require processing of large numbers of cells. For example, identification of a single cell with a distinct phenotype may only occur upon screening at least one million cells. As such, more valuable information may be obtained from faster screening of one microplate-supported sample rather than high throughput screening of many different samples.

In one example, the issues described above may be addressed by a sample holder for a multi-detector quantitative microscopy system, comprising a frame with a central opening, a pivotable arm positioned adjacent to the central opening and having a whippletree assembly at a first end of the pivotable arm, and a movable ram, in contact with a second end of the pivotable arm, the movable ram configured to pivot the pivotable arm. In this way, indexing of a microplate may be executed at a high frequency, thereby enabling capture of transient signal pathways for live specimens.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 11A shows a view of the plate holder with a mechanism for moving the plate holder in a first position.

FIGS. 2-16 are shown approximately to scale.

DETAILED DESCRIPTION

Figure 1:
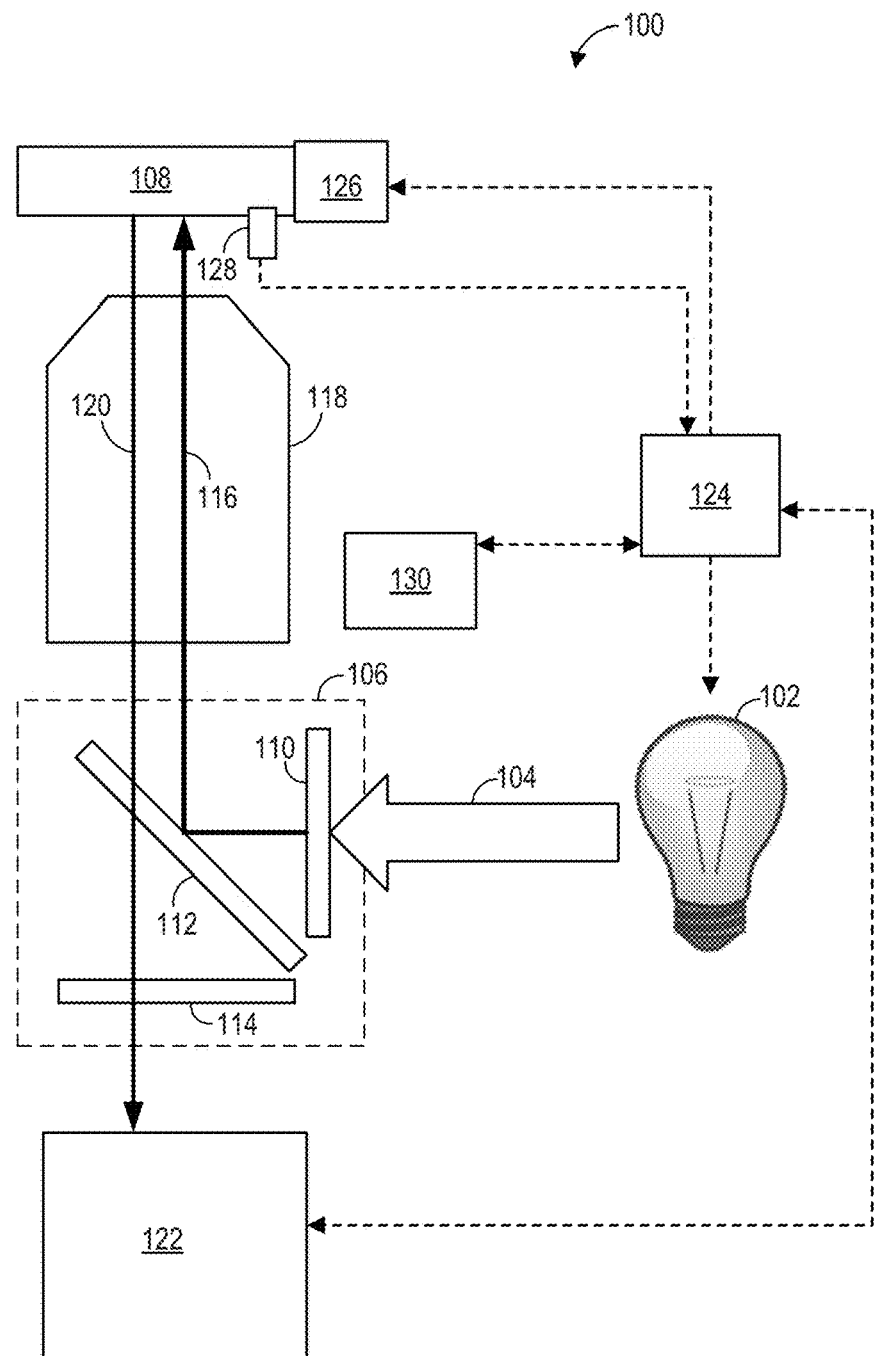
FIG. 1 shows a schematic diagram of a quantitative microscopy assembly.
Figure 2:
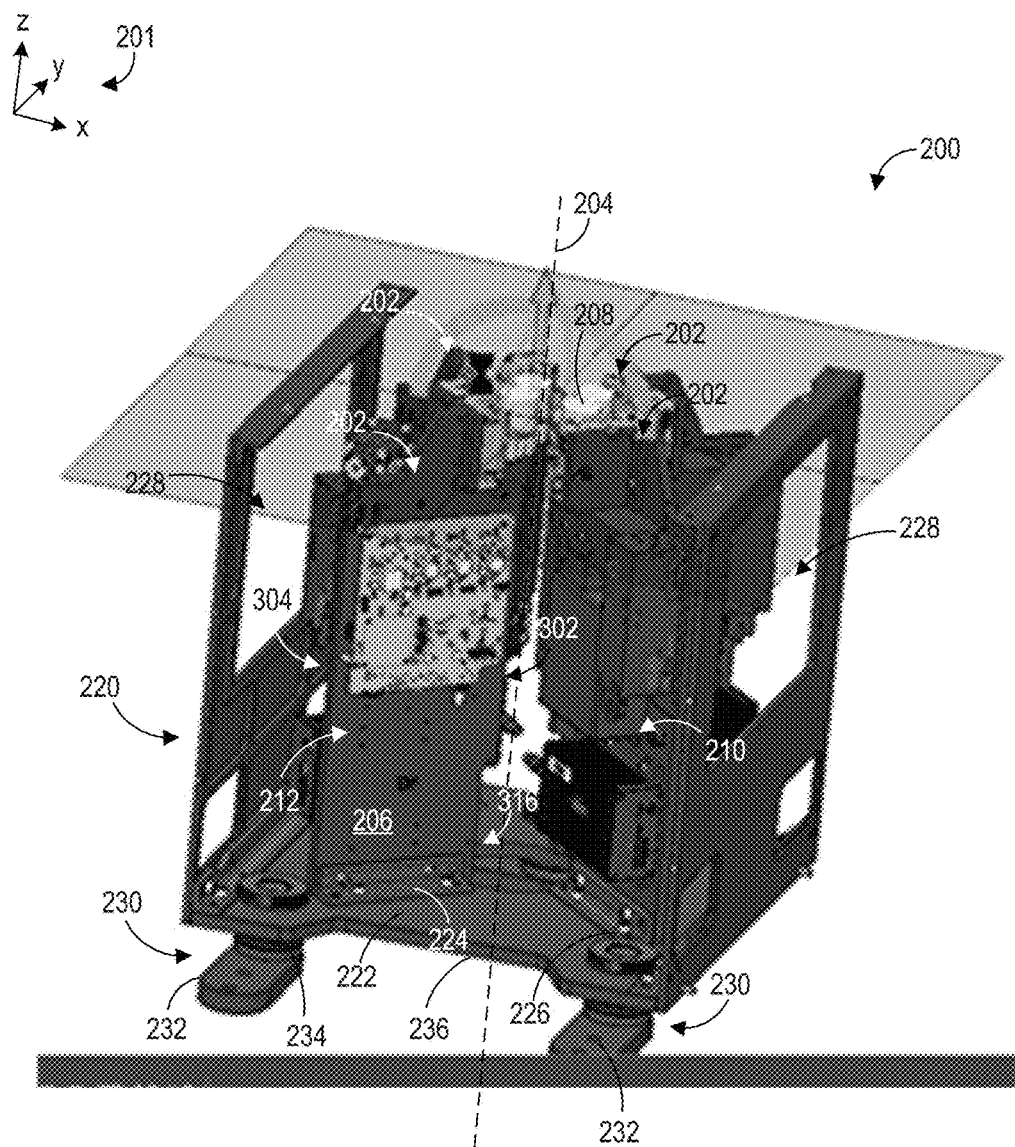
FIG. 2 shows a first perspective view of a multi-detector quantitative microscopy system.
Figure 3:
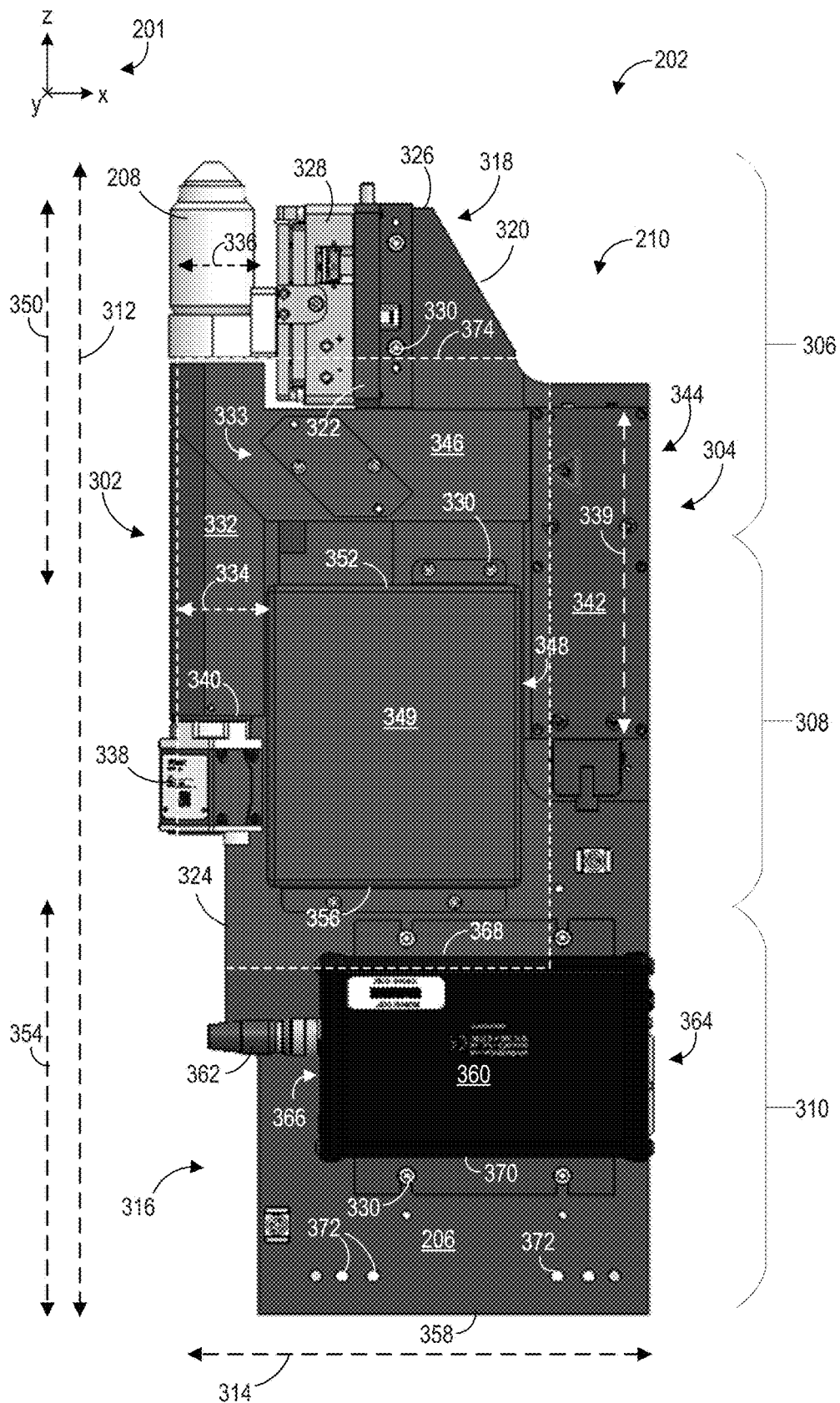
FIG. 3 shows a front view of a blade of the multi-detector quantitative microscopy system of FIG. 2.
Figure 4:
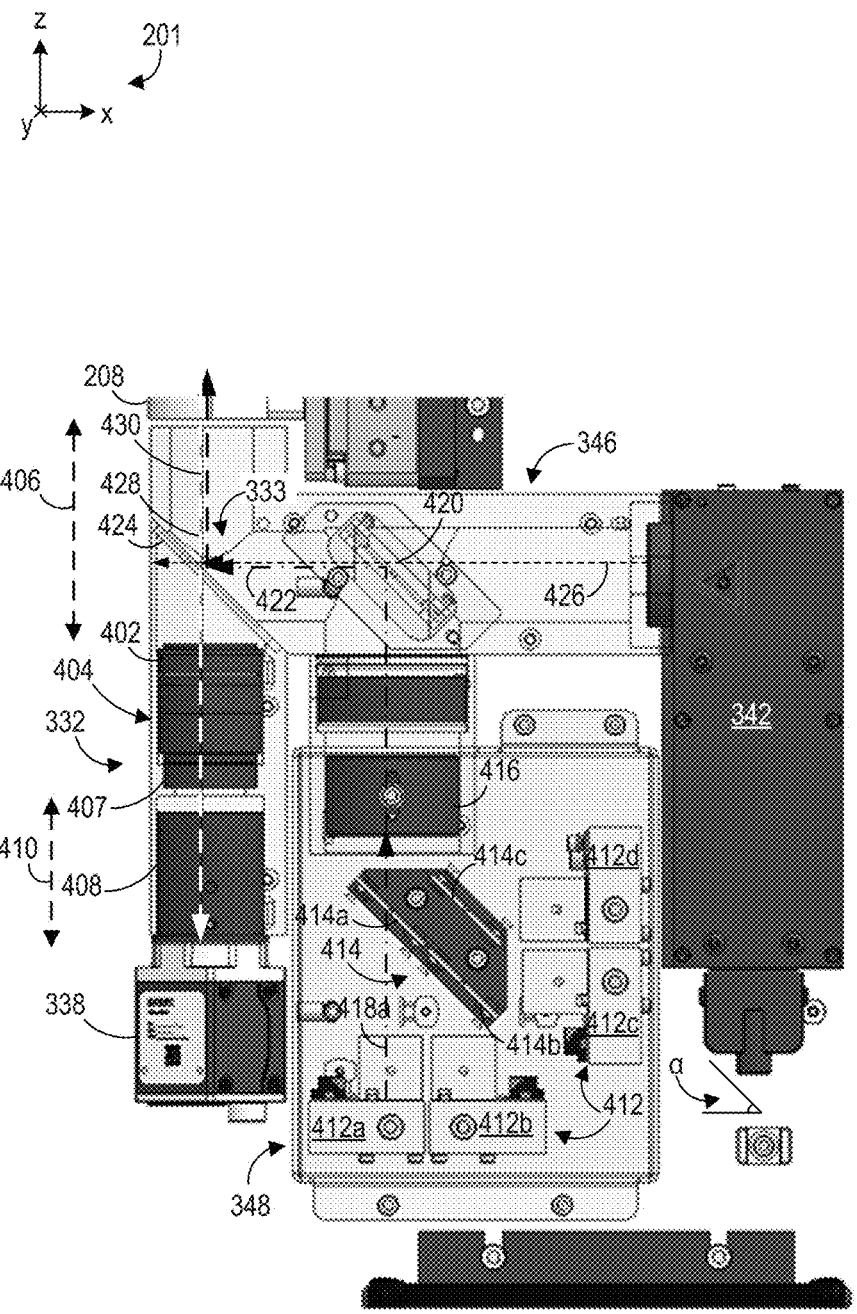
FIG. 4 shows a front view of inner components of the blade of FIG. 3.
Figure 5:
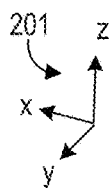
FIG. 5 shows a rear view of the blade.
Figure 5:
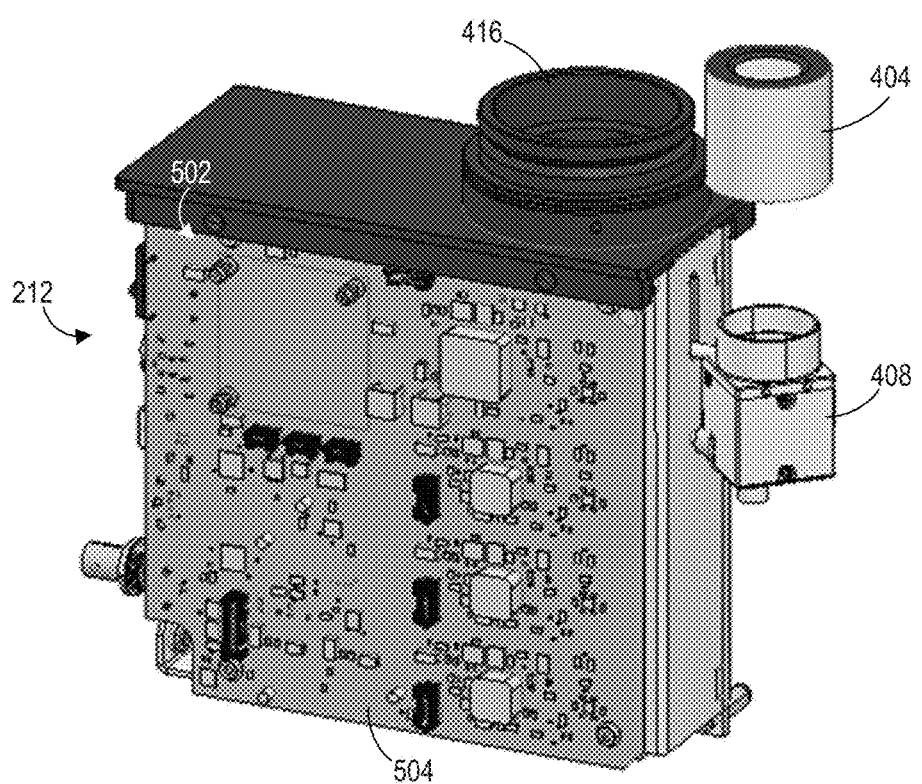
Figure 6:
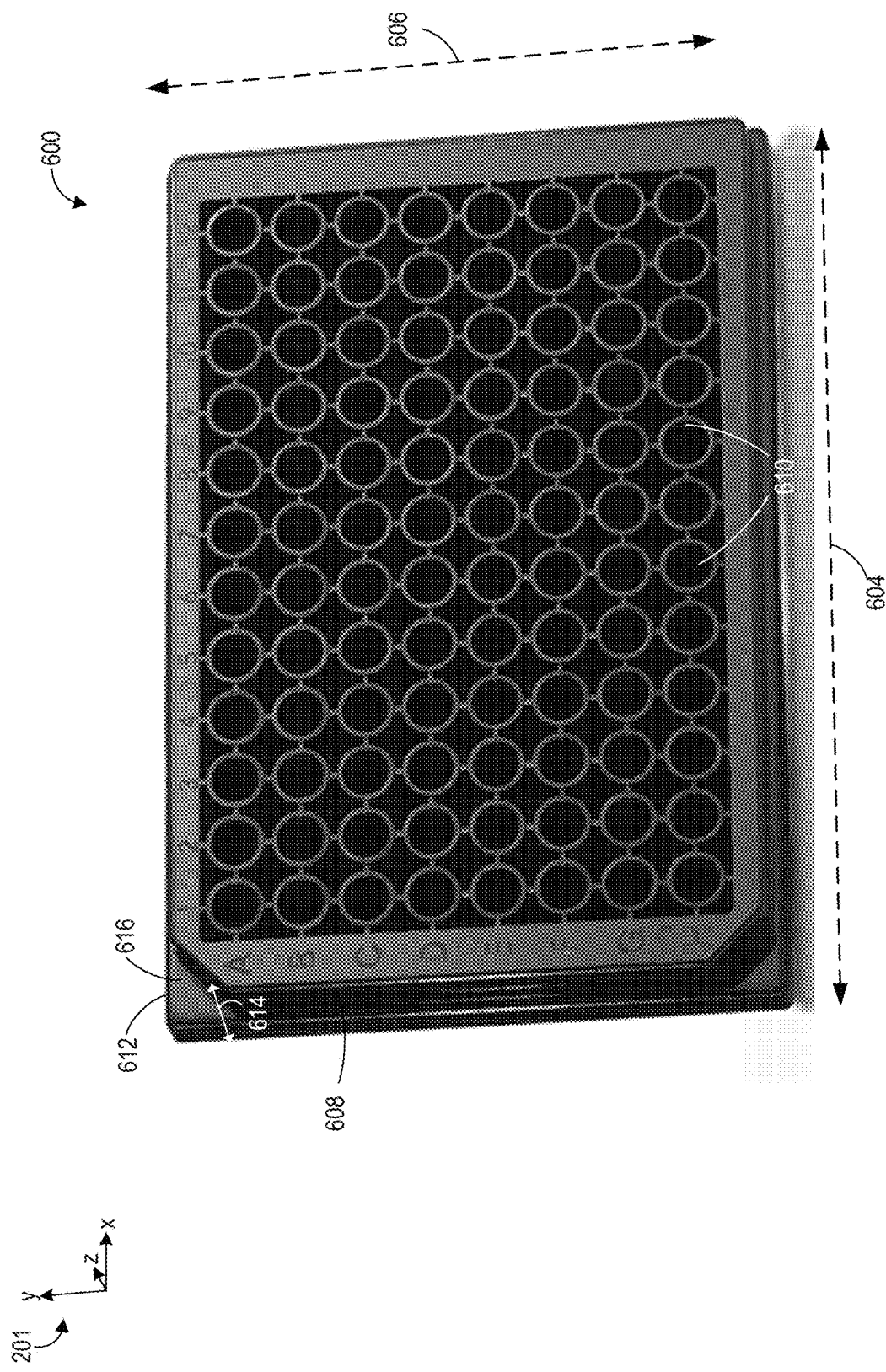
FIG. 6 shows an example of a microplate which may be used in the multi-detector quantitative microscopy system.
Figure 12:
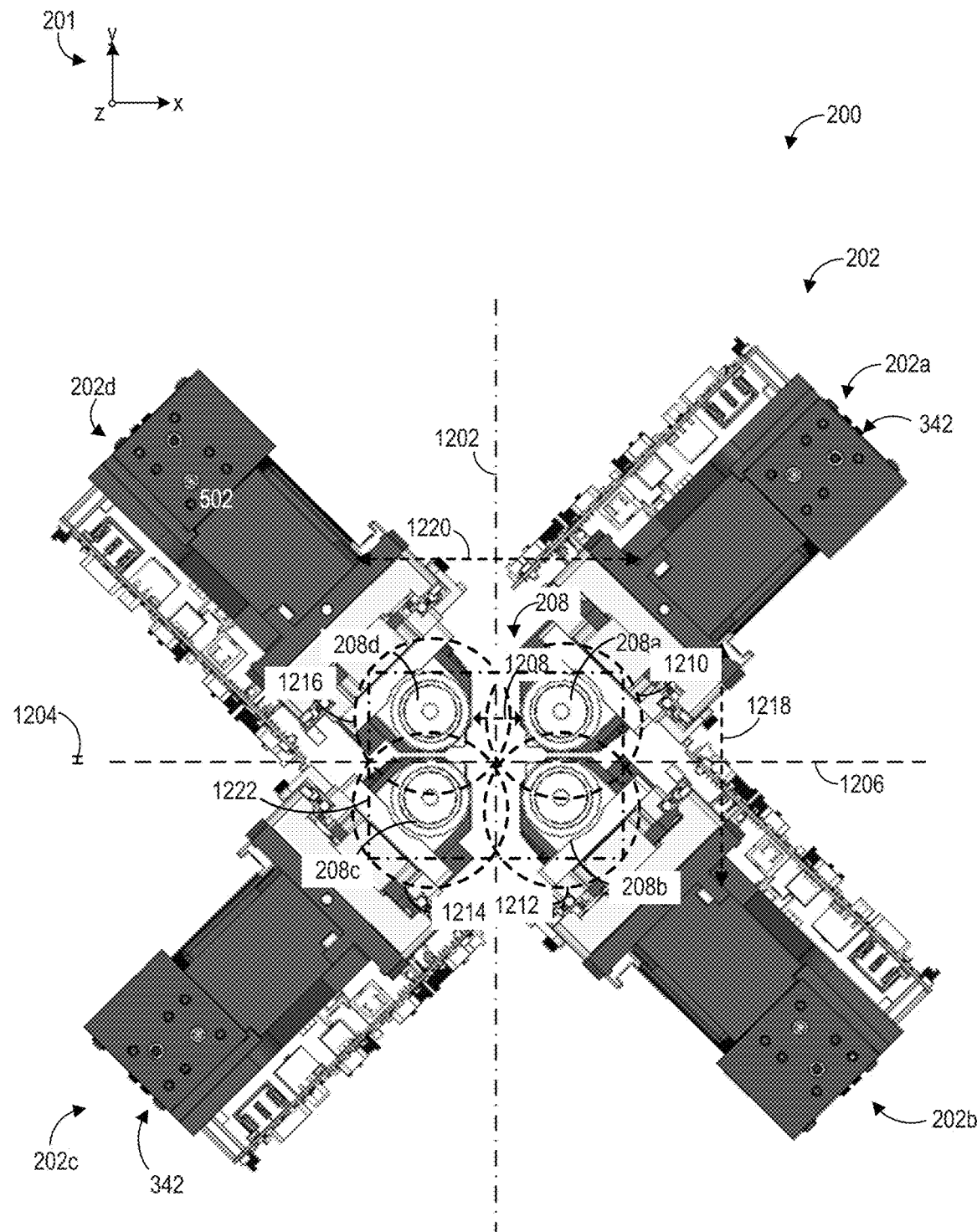
FIG. 12 shows a top view of the multi-detector quantitative microscopy system with the plate holder removed to show objectives of the multi-detector quantitative microscopy system.
Figure 13:
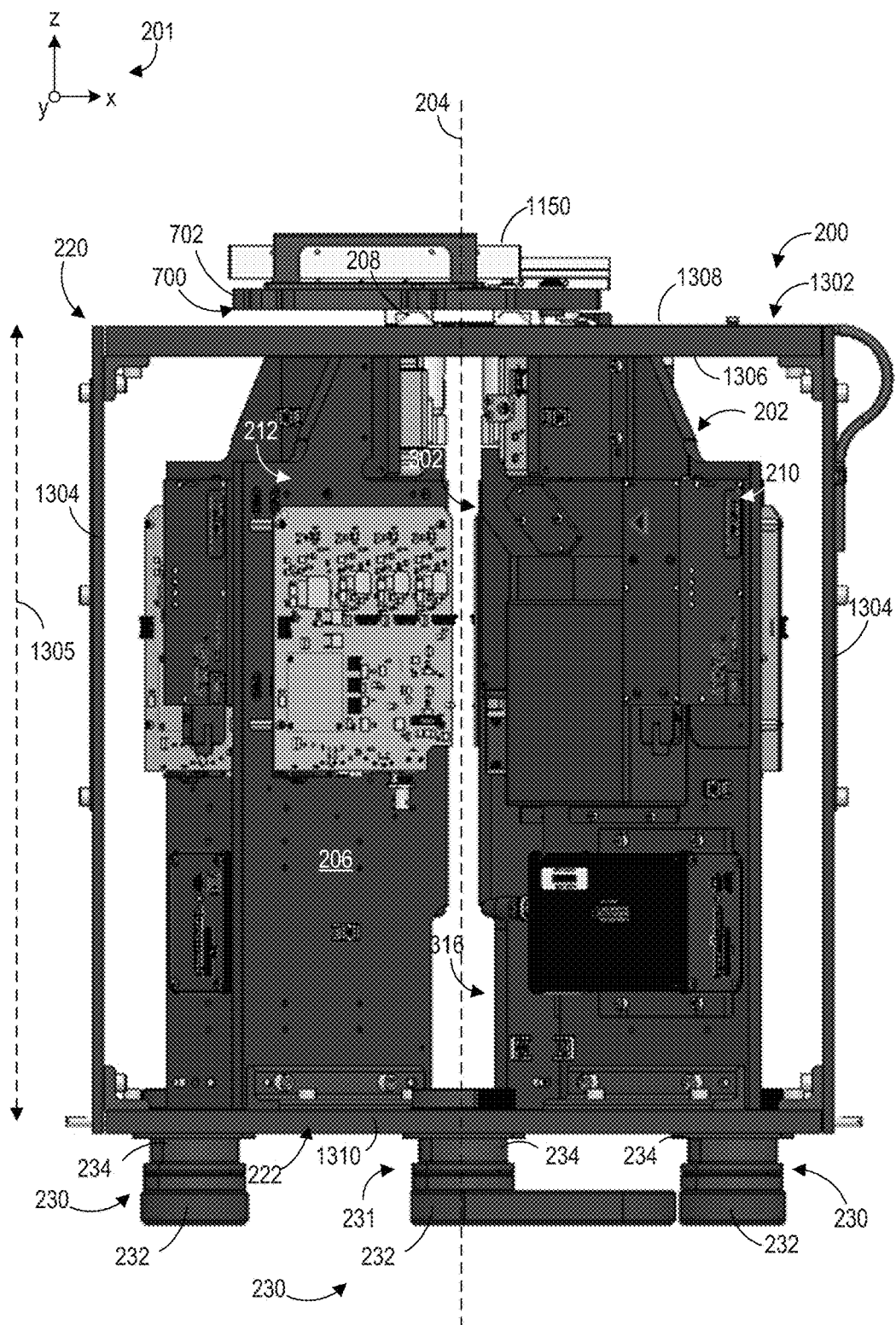
FIG. 13 shows a front view of the multi-detector quantitative microscopy system.
Figure 14:
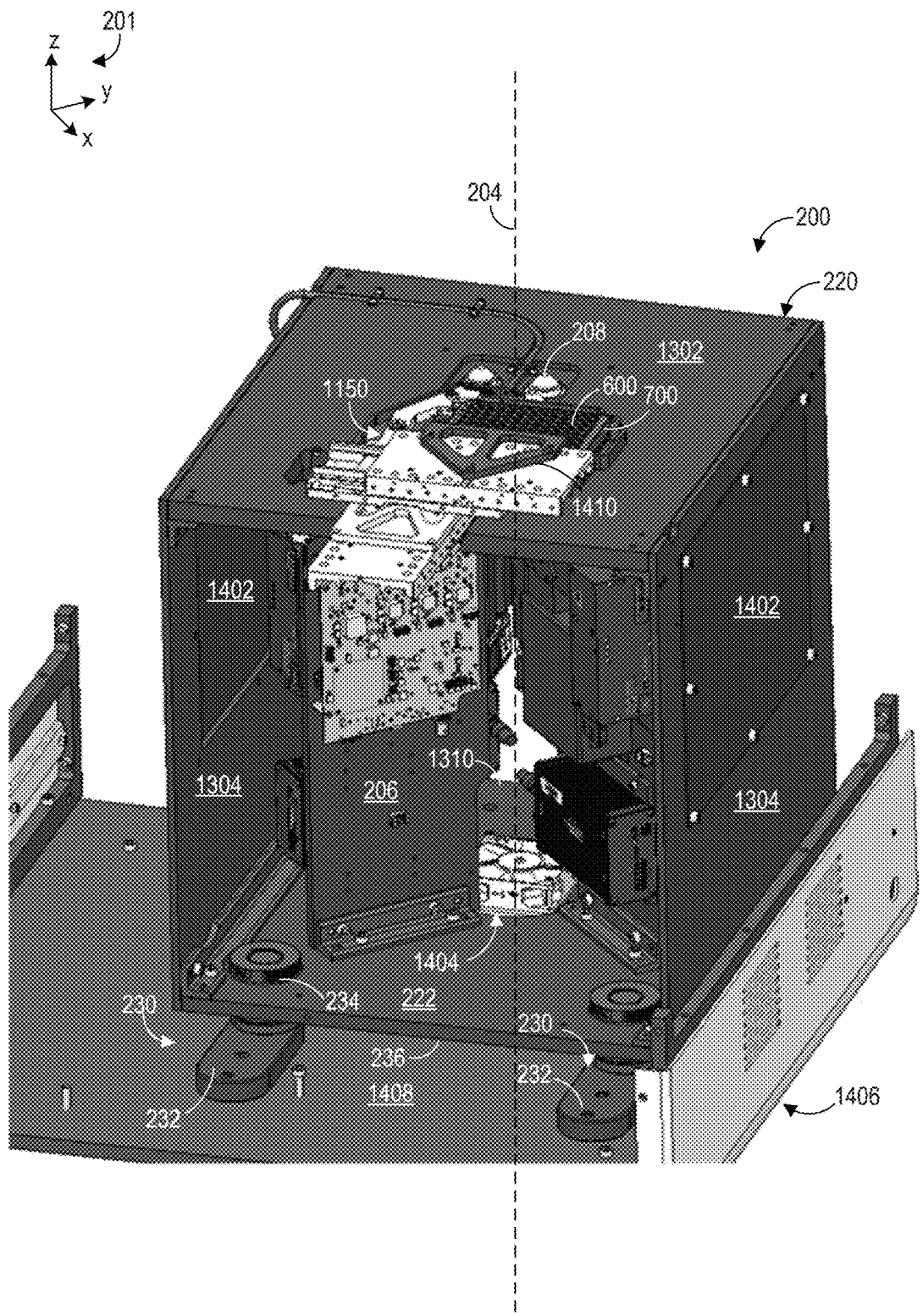
FIG. 14 shows a second perspective view of the multi-detector quantitative microscopy system.
Figure 15:
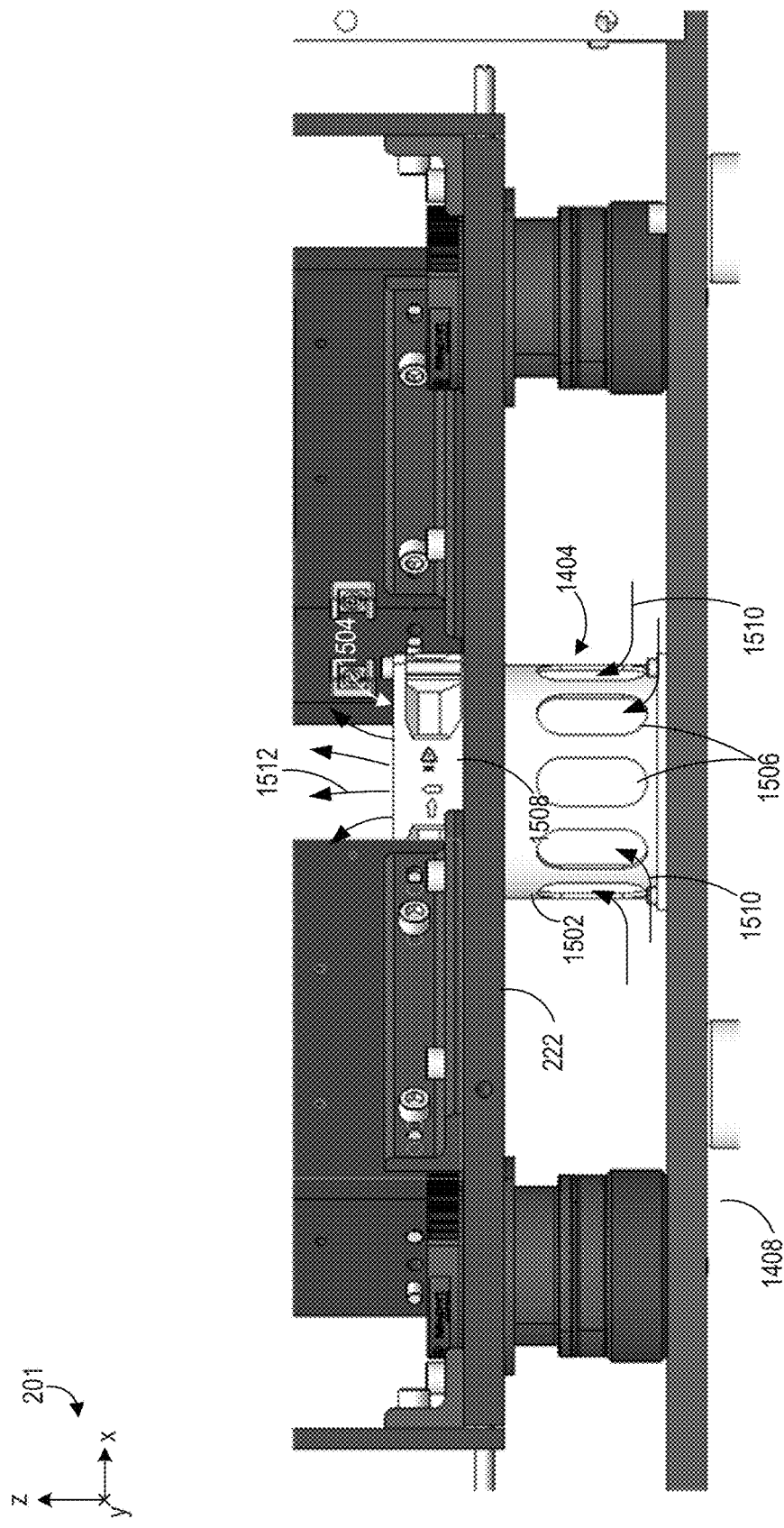
FIG. 15 shows a lower portion of the multi-detector quantitative microscopy system.
Figure 16:
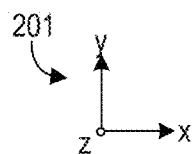
FIG. 16 shows a top view of a central fan of the multi-detector quantitative microscopy system.
Figure 16:
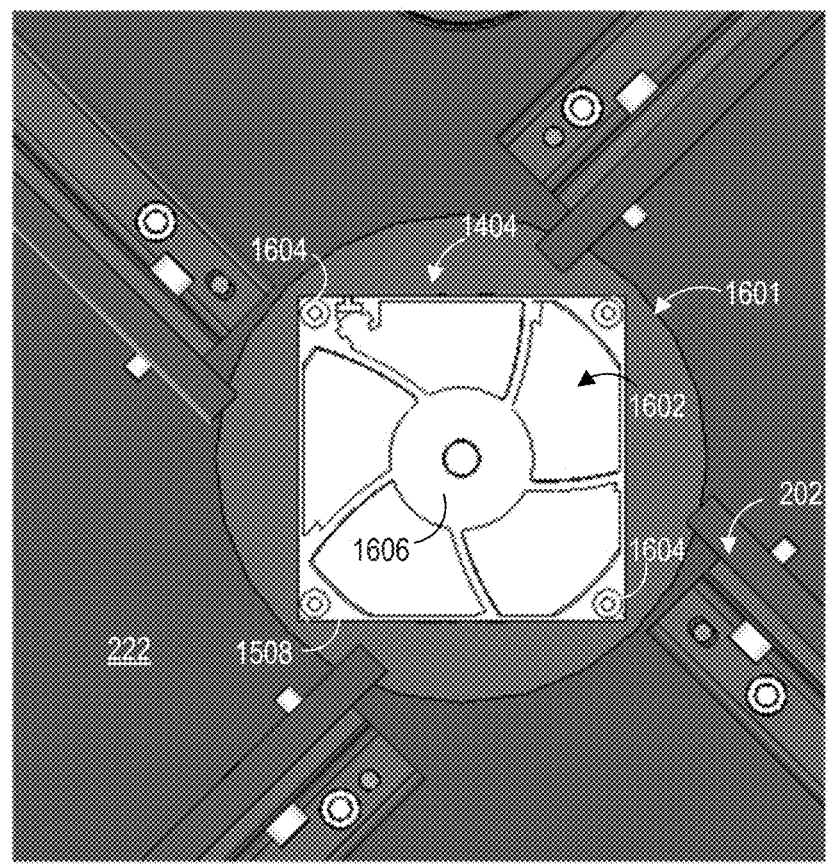
Figure 19:
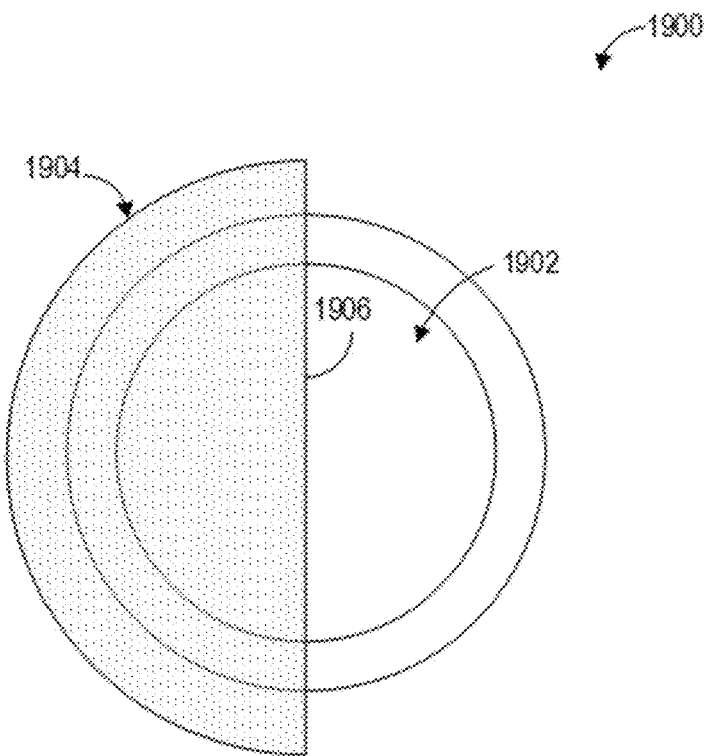
FIG. 19 shows an example of a conventional light shape used in an autofocus system for a microscope.
Figure 20:
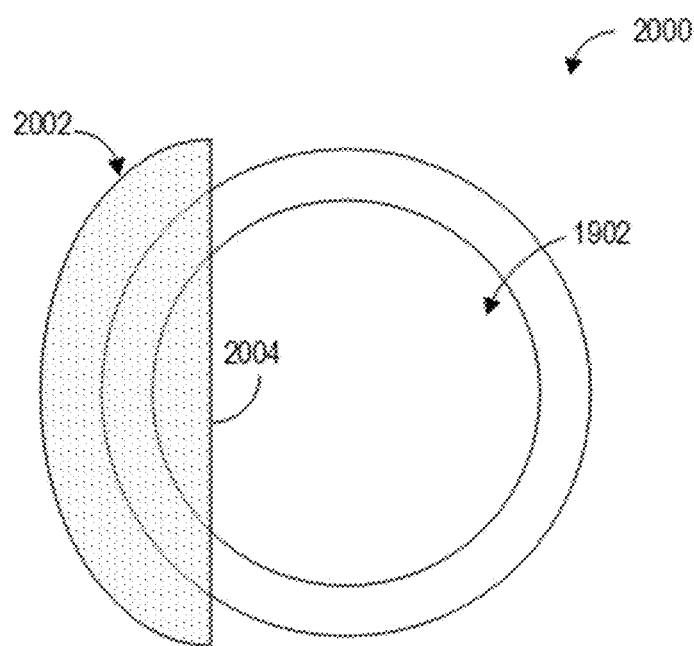
FIG. 20 shows an example of a light shape used in an autofocus system of the multi-detector quantitative microscopy system.

The following description relates to systems and methods for high throughput quantitative microscopy. Quantitative microscopy may be used to extract information from digital images by illuminating a sample with a desired wavelength, or range of wavelengths, of light. In one example, the wavelength may be selected to induce fluorescence from the sample which may be measured by a detector to provide a quantitative analysis of sample properties. An example of an assembly for quantitative microscopy is depicted in FIG. 1 as a schematic diagram. The assembly shown in FIG. 1 may be included in each of four blades of a multi-detector quantitative microscopy system, as shown in FIG. 2. Each of the blades includes an individual quantitative microscopy assembly and various views of one of the blades is shown in FIGS. 3-5, illustrating both external and internal components. The multi-detector quantitative microscopy system may be configured to collect images of samples which may be supported in a microplate, as depicted in FIG. 6. The microplate may be coupled to the multi-detector quantitative microscopy system by a plate holder, as shown in FIGS. 7-11B. A positioning of objectives at a top of the multi-detector quantitative microscopy system is shown in FIG. 12 and different views of the multi-detector quantitative microscopy system are illustrated in FIGS. 13-14. A cooling system of the multi-detector quantitative microscopy system may include a central fan as illustrated in FIGS. 15-16. The multi-detector quantitative microscopy system may utilize an autofocus system to focus the objectives relative to the microplate. Details of the autofocus system are shown, including a grid overlaid with a field of view of an objective at FIG. 17, a positioning of the objective relative to the microplate at FIG. 18, light shapes used for autofocusing at FIGS. 19-20, plots showing the focusing of the objective at FIGS. 21-22, and a method for the autofocusing at FIGS. 23-24. An example of a method for operating the multi-detector quantitative microscopy system to obtain images of the microplate is shown in FIGS. 25A-25B which further includes a method for synchronizing light sources of the multi-detector quantitative microscopy system to illuminate the microplate during image collection.

FIGS. 2-16 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Turning now to FIG. 1, a schematic diagram for a quantitative microscopy assembly 100 (hereafter, the assembly 100) is shown. In one example, the assembly 100 may be configured as a fluorescence microscopy assembly 100. However, various other types of analytical microscopic imaging techniques are possible, including but not limited to luminescence, colorimetry, etc. The assembly 100 of FIG. 1 includes a light source 102 providing incident light to components arranged in a path of the incident light, as indicated by arrow 104. The light source 102 may be a mercury-vapor lamp, a xenon arc lamp, a laser, or one or more light-emitting diodes (LEDs).

The incident light may be directed to a filter cube (or filter block) 106. The filter cube 106 may house components that filter the incident light such that target wavelengths are transmitted to a target to be analyzed, e.g., one or more samples supported on a sample holder 108. In one example, the sample holder 108 may be a microplate. Three filtering components are arranged in the filter cube 106, including an excitation filter 110, a dichroic filter 112, and an emission filter 114. The incident light may first pass through the excitation filter 110 which filters the light to allow only select, e.g., target, wavelengths to continue past the excitation filter 110. The target wavelengths may be wavelengths that excite electrons in specific fluorophores or fluorochromes, resulting in release of photons when the excited electrons relax to a ground state. The excitation light, e.g., light that has been filtered by the excitation filter 110, then strikes the dichroic filter (or dichroic beamsplitter) 112, as indicated by arrow 116. The dichroic filter 112 may be a mirror, for example, arranged at a 45 degree angle relative to an optical path of the assembly 100, e.g., angled at 45 degrees relative to the path of incident light indicated by arrow 104.

A surface of the dichroic filter 112 may include a coating that reflects the excitation light, e.g., light filtered by the excitation filter 110 but allows fluorescence emitted from the sample at the sample holder 108 to pass therethrough. The reflected excitation light, as indicated by arrow 116, passes through an objective 118 to illuminate the sample holder 108. If the sample fluoresces, light is emitted, e.g., generating emission light as indicated by arrow 120, and collected by the objective 118. The emission light passes through the dichroic filter 112 and continues to the emission filter 114 which blocks undesired excitation wavelengths. The filtered emission light is received at a detector 122. The detector 122 may be a camera, such as a charge-coupled device (CCD) camera, in one example. In other examples, the detector 122 may be another type of camera, for example, a CMOS camera, or a photomultiplier tube.

At the detector 122, the emission light may be converted into electronic data. For example, when the detector 122 is the CMOS camera, the detector 122 may include a light sensor configured as a transistor on an integrated circuit. Photons of the emission light may be incident on the light sensor and generate an electrical charge that is converted into electronic data representative of a photon pattern of the emission light captured within a field of view (FOV) of the camera. The electronic data may be stored at a memory of the camera, such as random access memory, and may be retrieved by a controller 124.

The controller 124 may be a computer, including various components such as a processor, input/output ports, an electronic storage medium for executable programs and calibration values, random access memory, a data bus, etc. The electronic storage medium can be programmed with computer readable data representing instructions executable by the processor for performing the methods described below as well as other variants that are anticipated but not specifically listed. The controller 124 may be coupled to various accessory devices including input devices such as a keyboard, a mouse, etc.

The controller 124 may be communicatively coupled to components of the assembly 100. For example, the controller 124 may be configured to command activation/deactivation of the light source 102 when prompted based on user input. As another example, the controller 124 may instruct adjustment of a position of the sample holder 108 to focus the excitation light on a different region of the sample holder. The controller 124 may command actuation of a motor 126 coupled to the sample holder 108 to vary the position of the sample holder 108 with respect to the objective 118 and the excitation light and provide instructions on how the sample holder position is to be modified. In some examples, a position sensor 128 may monitor the actual position of the sample holder 108 and may be communicatively coupled to the controller 124 to relay the sample holder position to the controller 124.

The controller 124 may also be communicatively coupled to the detector 122. As such, electronic data collected by the detector 122 may be retrieved by the controller 124 for further processing and display at an interface, such as a computer monitor. It will be appreciated that the controller 124 may be further coupled to other sensors and actuators of the assembly 100. In one example, communication between the controller 124 and the sensors and actuators of the assembly 100 may be enabled by various electronic cables, e.g., hardwiring. In other examples, the controller 124 may communicate with the sensors and actuators via a wireless protocol, such as Wifi, Bluetooth, Long Term Evolution (LTE), etc.

The assembly 100 may further include an auto-focus system 130, communicatively coupled to the controller 124. The auto-focus system 130 may utilize a sensor configured with a light source and optical elements for modifying and directing a light beam from the light source to the sample holder 108. An image may be generated based on reflection of the light beam which may be used by the controller 124 to determine a suitable adjustment of the objective and/or the sample holder 108 to align the focus of the objective with a target interface at the sample holder 108. In one example, the auto-focus system 130 may rely on a laser beam, as described below, with reference to FIGS. 17-23, and auto-focus algorithms implemented at the controller 124 to rapidly focus the assembly 100 on a desired area of the sample.

It will be appreciated that the assembly 100 depicted in FIG. 1 is a non-limiting example of a quantitative microscopy assembly. Other examples may include variations in quantities of individual components, such as a number of dichroic, excitation, and emission filters, a configuration of the light source, relative positioning of the components, etc. Specific examples of how the quantitative microscopy assembly may be arranged to increase throughput while providing high resolution results is described herein.

In one example, the quantitative microscopy assembly, e.g., the assembly 100 of FIG. 1, may be used for high frequency screening of biological samples. The microplate, supporting a plurality of specimens arranged in an array of wells of the microplate, may be positioned in a FOV of a detector of the assembly. Due to an inverse relationship between a size of the FOV and a magnification provided by the objective, the assembly may only obtain a high resolution image of a portion of the microplate with each image acquisition. In order to collect a complete data set of the plurality of samples, numerous image acquisitions may be demanded, delaying processing of the images and generation of analytical results. For applications such as drug screening, such delays may be costly.

In order to expedite image collection, a multi-detector quantitative microscopy system (hereafter, multi-detector system) may be used to rapidly obtain high resolution images of the microplate samples, thereby enabling faster screening. In particular, faster screening of a single microplate is enabled which provides increased resolution of time-dependent biological events for large screenings. Additionally, when applied to screening of live cells, more microplates may be processing within a smaller time period during which sample integrity is preserved. For kinetic assays, cycle times are faster, allowing the microplates to be analyzed multiple times.

A configuration of the multi-detector system may be influenced by dimensions of the microplate which affects a positioning of a plurality of objectives of the multi-detector system. For example, a spacing between the plurality of objectives may be maintained within a target distance to optimize respective overlapping of FOVs to generate a cohesive, continuous, and complete image. Furthermore, the spacing of the plurality of objectives allows each detector of the multi-detector to be actively collecting images during every imaging event. In some examples, the detectors may be configured to obtain different types of data, thus expanding a capability of the multi-detector system to capture new and unprecedented information. An arrangement of remaining components of the multi-detector system may be thus configured to accommodate the spacing and orientations of the plurality of objectives relative to the microplate. Furthermore, it may be desirable to maintain a footprint of the multi-detector system as small as possible.

In one example, as shown in FIG. 2, a multi-detector system 200 may be formed of four individual blades 202 arranged in an x-shaped configuration. The multi-detector system 200 is depicted in FIG. 2 with an upper portion of the system and portions of a housing 220 of the multi-detector system 200 omitted for clarity. The upper portion may include a top plate of the housing 220 of the multi-detector system 200 as well as a sample receiving assembly. A set of reference axes 201 is provided, indicating a y-axis, an x-axis, and a z-axis. In one example, the z-axis may be parallel with a direction of gravity. Furthermore, a central axis 204 of the multi-detector system 200 may be parallel with the z-axis. Each blade 202 of the multi-detector system 200 may include at least the components depicted in the assembly 100 of FIG. 1 and the blades 202 may be operated concurrently to collect image data in parallel. Each blade 202 therefore forms an individual quantitative microscopy assembly. The components arranged in each of the blades 202 may be positioned to optimize both an FOV of an objective of each blade and a magnification/resolution of the resulting images. As such, the components may be arranged in a vertical orientation, e.g., as a stack along each blade.

For example, each blade 202 of the multi-detector system 200 may be similarly configured, including a vertically oriented plate 206 supporting a variety of components. An objective 208, which may be an embodiment of the objective 118 of FIG. 1, may be positioned at a top of each blade 202 with other components of each blade 202 arranged below the objective 208, with respect to the z-axis. The blade 202 may have a front side 210 and a back side 212 and the front side 210 of the blade 202 is depicted in greater detail in FIG. 3.

The multi-detector system 200 may offer several advantageous over conventional systems. For example, conventional systems may employ multiple detectors to enable parallel imaging of microplates, thereby increasing throughput. However, the conventional systems may not enable a higher imaging frequency of a single microplate. As a result of a packaging of the multi-detector system 200, and in particular, an arrangement of the objectives 118 at an upper portion of the multi-detector system 200, below the microplate, the quantitative microscopy assemblies of the multi-detector system 200 may synchronously capture images of portions of the microplate. The images may be combined to form a complete image of the microplate, thus expediting a speed at which each well of the microplate is indexed. The packaging of the multi-detector system 200 allows the multi-detector system 200 to have a similar footprint to a system with only one quantitative microscopy assembly.

Furthermore, in one example, the high speed imaging provided by the multi-detector system 200 may allow the multi-detector system 200 to be used for imaging live biological specimens in addition to endpoint assays. In addition to the imaging speed, a fast framerate and high cycling frequency of the multi-detector system 200 enables new observations of biology, such as live events and transient cell signals, which may otherwise be challenging to obtain using the conventional systems. As a result, cellular models may be constructed with greater accuracy.

In addition, the arrangement of the objectives enables both high speed imaging of the microplate and efficient packaging of other components of the quantitative microscopy assemblies, such as a detector and a light source, to minimize the footprint of the multi-detector system 200. The objectives may be positioned relative to one another with a target distancing or spacing therebetween that accommodates a specific geometry of the microplate and reduces instances where a focus of any of the objectives migrates outside of a target imaging region of the microplate. A resulting capability of the objectives to rapidly capture images of the microplate in a synchronized manner may not be readily replicated with other arrangements of the objectives.

In some examples, the multi-detector system 200 may be further configured with environmental control capabilities. For example, the microplate may be enclosed within a sealed structure such that exposure of the sample to temperature, humidity, carbon dioxide level, etc., may be regulated. Furthermore, the multi-detector system 200 may be adapted with a rapid, automated microplate changing mechanism, such as an automated robotic arm.

Turning now to a view, as shown in FIG. 3, of the front side 210 of the blade 202, the blade 202 has two vertical sides, e.g., parallel with the z-axis, including an inner side 302, e.g., proximate to the central axis 204 as shown in FIG. 2, and an outer side 304 that is distal to the central axis 204. The blade 202 may have an upper region 306, a middle region 308 and a lower region 310, the upper region 306 positioned above the middle region 308 and the middle region 308 positioned above the lower region 310, along the z-axis. Each region may form a similar portion of a height 312, as defined along the z-axis, of the blade 202. The blade 202 may have a generally rectangular geometry with a width 314 that is smaller, e.g., of a lesser distance, than the height 312.

As described above, the blade 202 may be formed of a plate 206 which is a structural support to which a variety of components may be coupled. The plate 206 may therefore be formed of a rigid, durable material such as aluminum, another type of metal, plastic, etc. Edges of the plate 206 may include sections configured to support specific components of the quantitative microscopy assembly and of the multi-detector system 200. For example, the plate 206 may include a notched section 316 along the inner side 302 of the blade 202 in the lower region 310 such that the width 314 of the blade 202 at the lower region 310 is narrower that along the middle region 308 and the upper region 306.

Furthermore, the plate 206 may include a protrusion 318 extending upwards, with respect to the z-axis, and positioned at a mid-region along the width 314 of the blade 202. The plate 206 may be narrowest at the protrusion 318. The protrusion 318 may be generally triangular with a sloped edge 320 (e.g., sloped relative to the y-axis), and a straight edge 322 that is parallel with the z-axis. Various casings and covers may be coupled to the plate 206 via fasteners, such as screws, bolts, etc., to shield and cover components of the quantitative microscopy assembly.

At the upper region 306 of the blade 202, the objective 208 may be attached to the plate 206 along the inner side 302 such that the objective 208 is aligned parallel with an inner edge 324 of the plate 206 at the upper region 306 but protrudes beyond the inner edge 324 in an inwards direction (e.g., towards the central axis 204 shown in FIG. 2) along the x-axis. As such, the objective 208 may be located at an upper left-hand corner (when viewing the front side 210 of the blade 202) of the blade 202 and may also protrude above a top edge 326 of the plate 206 at the protrusion 318. Furthermore, the objective 208 may be adjustable to translate along the z-axis to allow focusing of an image projected by the objective 208. Translation of a position of the objective 208 along the z-axis may be enabled by a motor, e.g., as included in an objective module 328 and described further below, or may be adjusted manually.

The objective 208 may be a substantially cylindrical component formed of a plurality of lenses enclosed within a barrel, the plurality of lenses configured to provide a target magnification of an image. The objective 208 may thus have a specific magnification and numerical aperture (NA), where the NA is a value indicating a range of angles over which the objective 208 can accept or emit light. The objective 208 is a component of the quantitative microscopy assembly positioned closest to (and below) a sample and may gather light from the sample and focus the light to produce an image. As magnification provided by the objective 208 increases, a field-of-view (FOV) of the objective 208 decreases. In one example, the objective 208 may include fixed focus lenses and may be therefore used at a specific working distance, such as a distance between 0.5-2 mm.

The objective 208 may be attached to the plate 206 by the objective module 328 extending between the objective and the protrusion 318 of the plate 206. The objective module may include a bracket fixedly coupling the objective 208 to the objective module 328, an objective mover which may be a motor that adjusts the position of the objective 208 along the z-axis, as well as a position sensor to monitor the position of the objective along the z-axis. The objective mover may be controlled, e.g., activated/deactivated, by a controller such as controller 124 of FIG. 1. The objective module 328 may be attached to the plate 206 by a plurality of fasteners 330 which may also be used to secure other components to the plate 206. A first optical passage 332 may extend vertically (e.g., along the z-axis) directly below the objective 208 and may have a cylindrical housing coupled to the plate 206, also via the plurality of fasteners 330. The first optical passage 332 may enclose microscope components, described further below with reference to FIG. 4, and may be an embodiment of the filter block 106 of FIG. 1.

The first optical passage 332 may extend from a midpoint from below the objective 208 in the upper region 306 of the blade 202 to a mid-point along the height 312 of the blade 202 in the middle region 308. An outer diameter 334 of the first optical passage 332 may be larger than an outer diameter 336 of the objective 208. A camera 338, which may be an embodiment of the detector 122 of FIG. 1, may be coupled to a bottom end 340 of the first optical passage 332.

In one example, the camera 338 may be a CCD camera configured to convert an electrical signal into optical image or video using a CCD. In another example, the camera 338 may be a complementary metal oxide semiconductor (CMOS) camera which utilizes metal oxide semiconductors to convert light into electrical signals. The camera 338 may be positioned to receive emission light from an illuminated sample to allow analysis of an image generated by the camera 338, the emission light delivered from the sample to the camera 338 via the objective 208 and the first optical passage 332. The camera 338 is thereby optically coupled to the objective 208 by the first optical passage 332. The camera 338 may be mounted at the bottom end 340 of the first optical passage 332 and maintained in place by a bracket or some other supporting mechanism.

The plate 206 of the blade 202 may also support a laser auto-focus (LAF) sensor 342 arranged proximate to the outer side 304 of the blade 202. The LAF sensor 342 may be enclosed in a rectangular cover secured to the plate 206 by fastening devices, such as the plurality of fasteners 330 or some other fastening mechanism. The LAF sensor 342 may emit a laser beam into an optical path of the quantitative microscopy assembly, such that the LAF sensor 342 may use the laser beam as an optical probe to determine a focus of the quantitative microscopy assembly. In one example, the LAF sensor 342 may be configured to produce a 785 nm red laser beam from a light source such as a laser diode. The laser beam may be reflected from a surface of the sample or a surface of a sample holder (e.g., a microplate) and return to the LAF sensor 342 as an optical signal which may be used to assess a focus of the quantitative microscopy assembly.

The LAF sensor 342 may be positioned such that a longest dimension of the LAF sensor 342, e.g., a length 339 of the LAF sensor 342, is parallel with the height 312 of the blade 202. By positioning the LAF sensor 342 as shown in FIGS. 3 and 4, a footprint of the blade 202 is maintained small. Furthermore, the positioning of the LAF sensor 342 enables a geometry of an optical path, e.g., the first optical passage 332 and a second optical passage 346, described below, to be maintained small, e.g., a length of each passage is configured to be as short as possible.

The LAF sensor 342 may be oriented parallel with and spaced away from the first optical passage 332, extending along a portion of the height 312 of the plate 206, between a mid-point along the upper region 306 and a mid-point along the middle region 308. A plurality of optical elements may be included in the LAF sensor 342, including a light source for generating the laser beam and a detector for receiving the reflected laser beam which may be processed by an LAF controller (described below). In one example, the detector may be configured as a CCD or a CMOS detector. The plurality of optical elements may further include a focal plane array, one or more lenses, an aperture stop, a beam splitter, etc. The laser beam may thereby be directed and shaped by the plurality of optical elements to generate the optical signal used to align the focus of the quantitative microscopy assembly.

The LAF sensor 342 may transmit the laser beam at a top end 344 of the LAF sensor 342 in a direction perpendicular to an optical path of the first optical passage 332. For example, the second optical passage 346 may extend horizontally, e.g., along the x-axis, between the top end 344 of the LAF sensor 342 and the first optical passage 332, and may merge with the first optical passage 332 at an intersection 333. The second optical passage 346 may be enclosed in a casing with flat surfaces, the casing attached to the plate 206 by the plurality of fasteners 330 or other fastening devices and may merge continuously with the first optical passage 332 such that the first and second optical passages 332, 346 are optically coupled. The laser beam emitted by the LAF sensor 342 may thereby pass through the second optical passage 346 and merge with excitation light. As the laser beam passes through the second optical passage 346, the laser beam may interact with components enclosed within the first and second optical passages 332, 346 that facilitates deflection and transmission of the laser beam and excitation light, as described further below.

A geometry and positioning of the first optical passage 332 and the second optical passage 346 may allow the optical passages to be shorter in length than a conventional system (e.g., a system without vertical arrangement of microscope assemblies). An overall optical path of each blade 202 of the multi-detector system 200 is therefore miniaturized, allowing the assembly to have smaller packaging demands and increasing an efficiency of incident light transmission to a sample.

The blade 202 may also include a light source 348, which may be an embodiment of the light source 102 of FIG. 1, enclosed by a cover 349 that is secured to the plate 206 by the plurality of fasteners 330. Details of the light source 348 are shown in FIG. 4 and described further below. The cover 349 of the light source 102 may occupy a portion of the width 314 of the blade 202 similar to a distance between the first optical passage 332 and the LAF sensor 342, and the cover 349 of the light source 102 may have a rectangular outer geometry. The light source 348 may be positioned in a central region of the plate 206 such that the light source 348 (and the cover 349) is spaced away from all edges of the plate 206. In one example, a first distance 350 between the top edge 326 of the plate 206 and a top edge 352 of the cover 349 of the light source 348 may be less than a second distance 354 between a bottom edge 356 of the cover 349 and a bottom edge 358 of the plate 206. However, in other examples, the first distance 350 and the second distance 354 may be similar or the first distance may be greater than the second distance 354.

An LAF controller 360 may be arranged below, e.g., with respect to the z-axis, the light source 348 and the LAF sensor 342. The LAF controller 360 may be a rectangular structure and may include various electronic components for signal processing, operation of the LAF sensor, monitoring a status of the LAF sensor, etc., and adapted with a connector 362 to allow coupling of a cable to the LAF sensor 342. The cable may enable communication between the LAF sensor and the LAF controller 360. The LAF controller 360 may include a plurality of ports along an outer end 364 of the LAF controller 360 to allow the LAF controller 360 to be connected to, for example, a system controller, such as the controller 124 of FIG. 1.

Connectivity between the LAF controller and the system controller may allow a position of the objective 208 to be adjusted based on an alignment of the quantitative microscope assembly focus with a target focal plane as detected by the LAF sensor 342. For example, when the focus is determined to be out of alignment with the target focal plane, the LAF controller 360 may inform the system controller of an amount of offset of the focus from the target focal plane. In response to the information from the LAF controller 360, the system controller may command adjustment of the objective 208 by activating the objective mover of the objective module 328 and modifying the position of the objective 208 along the z-axis accordingly.

The LAF controller 360 may be mounted onto brackets which allow the LAF controller 360 to be secured to the plate 206 by the plurality of fasteners 330. The outer end 364 of the LAF controller 360 may be aligned and flush with the outer side 304 of the blade 202 (and of the plate 206) and an inner end 366 of the LAF controller 360 may be spaced away from the inner edge 324 of the plate 206. An upper side 368 of the LAF controller 360 may be spaced away from the bottom edge 356 of the cover 349 of the light source 348 and a bottom side 370 of the LAF controller 360 may be spaced away from the bottom edge 358 of the plate 206.

The plate 206 may further include a plurality of apertures 372 arranged between the LAF controller 360 and the bottom edge 358 of the plate 206. As shown in FIG. 3, the plurality of apertures 372 may be aligned along the axis and separated into two groups, each with three apertures. Fasteners may be inserted through the plurality of apertures 372 to attached the plate 206 to a mounting device, such as a bracket, used to couple the plate 206 to a base, e.g., the base 222 of FIG. 2, of the multi-detector system 200.

A region of the blade 202, indicated by a dashed rectangle 374 in FIG. 3, is illustrated in FIG. 4 with select covers, housings, and casings removed to reveal shielded inner components. For example, as depicted in FIG. 4, the cover 349 (e.g., as shown in FIG. 3) of the light source 348 is removed, as is the housing of the first optical passage 332 and the casing of the second optical passage 346. The plate 206 is omitted in FIG. 4 for brevity. Turning first to the first optical passage 332, an emission filter 402 may be arranged in the first optical passage 332 proximate to the intersection 333 of the first optical passage 332 and the second optical passage 346. The emission filter 402 may be an example of the emission filter 114 of FIG. 1, configured to remove undesired wavelengths from emission light travelling from the objective 208 to the camera 338. Materials from which the emission filter 402 may be formed include colored glass, glass with a dielectric optical coating for a specific wavelength, acrylic, etc., and may be configured with longpass or bandpass transmission.

The emission filter 402 may be directly coupled to a tube lens 404 such that light filtered by the emission filter 402 immediately passes through the tube lens 404. In one example, as shown in FIG. 4, the emission filter 402 may be attached to the tube lens 404 to form a single unit. For example, the emission filter 402 may include a frame with a fitting configured to have a press-fit connection or threaded connection to mate with a similar connection at the tube lens 404.

The tube lens 404 may have optical properties configured to complement optical properties of the objective 208. The tube lens 404 is separated and spaced away from the objective 208 by a distance 406. In one example, the distance 406 may be between 50-200 mm. In a second example, the distance 406 may be between 85-90 mm. However, other distances are possible. The tube lens 404 may be decoupled from the objective 208 to allow variable pairing of tube lens focal length with objective magnification to achieve a desired balance between resolution and FOV. For example, a conventional system may utilize an objective 208 with a 20× magnification in conjunction with a 200 mm focal length tube lens. In the quantitative microscopy assembly described herein, the tube lens 404 may instead have a 100 mm focal length and, when combined with the 20× magnification provided by the objective 208, allows the quantitative microscopy assembly to have both a larger FOV and higher resolution than the conventional system. The decoupled pairing of the objective 208 and the tube lens 404 may contribute at least partially to a higher throughput of the multi-detector system by increasing the FOV of each objective of the system and thereby generating an image from a larger section of a microplate while capturing fine details within the imaged portion.

A bottom end 407 of the tube lens 404 may be connected to a camera mount 408 which couples the camera 338 to the tube lens 404 and maintains the position of the camera 338. For example, camera 338 may have a threaded engagement with the camera mount 408. The camera mount 408 may be similarly coupled to the tube lens 404 and may have a length 410 configured to dissipate heat between the tube lens 404 and the camera 338. As such, the camera mount 408 may also be a thermal isolator and may assist in thermal management at the camera 338. For example, any heat generated by interaction of the emission light with the emission filter 402 and/or tube lens 404 may be absorbed by the camera mount 408.

The camera mount 408 may be formed of a plastic with insulating properties. By attaching the camera 338 to the first optical passage 332 by way of the camera mount 408, the camera 338 does not directly contact metallic components of the quantitative microscopy assembly. For example, the camera 338 does not contact the housing of the first optical passage 332, or the tube lens 404, which may be formed of or include parts formed of a metal such as aluminum. Furthermore, the camera is spaced away from the plate 206 and the cover 349 (as shown in FIG. 3) of the light source 348, which may also be formed of a metal such as aluminum, stainless steel, etc. The camera 338 is therefore isolated from heat conducting materials of the quantitative microscopy assembly.

The light source 348 includes light-emitting diodes (LEDs) 412 arranged around a set of dichroic mirrors 414. The LEDs includes a first LED 412a, a second LED 412b, a third LED 412c, and a fourth LED 412d. The first and second LEDs 412a, 412b may be adjacent to one another and aligned along the x-axis and positioned proximate to a lower (with respect to the z-axis) end of the light source 348. The first LED 412a may be closer to the camera 338 than the second LED 412b. The third LED 412c and the fourth LED 412d may be aligned along the z-axis and positioned adjacent to one another along a side of the light source 348 proximate to the LAF sensor 342. The fourth LED 412d may be arranged above the third LED 412c. The first and second LEDs 412a, 412b form a first group of the LEDs that is oriented perpendicular to a second group of the LEDs, formed of the third and fourth LEDs 412c, 412d.

Each of the LEDs 412 may be configured to emit light of different wavelengths. For example, the first LED 412a may have a center wavelength of 630 nm, the second LED 412b may have a center wavelength of 470 nm, the third LED 412c may have a center wavelength of 390 nm, and the fourth LED 412d may have a center wavelength of 555 nm. However, other center wavelengths may be possible. During sample imaging, each of the LEDs 412 may be individually activated to illuminate the sample with different wavelengths of light, according to which of the LEDs 412 is activated. A separate image of the sample may be obtained from each illumination channel of the LEDs 412 which provides images depicting variations in sample fluorescence depending on the center wavelength of the incident light.

By directly coupling the light source 348 to the blade 202, rather than positioning the light source external to the blade 202 and distal to other imaging components supported on the plate 206, an illumination provided by the light source 348 may be brighter. As a result, shorter exposure times are enabled which may lead to increased imaging speed. In other examples, the light source 348 may instead be coupled by an optical cable, fiber optics, etc., but, as such, may provide less bright illumination.

The set of dichroic mirrors 414 may be arranged in an area between the first and second groups of the LEDs and includes a first dichroic mirror 414a, a second dichroic mirror 414b, and a third dichroic mirror 414c. The first and second dichroic mirrors 414a, 414b may be aligned along a common axis that is angled relative to the alignment of the first group of the LEDs 412 as well as to the alignment of the second group of the LEDs 412. The third dichroic mirror 414c is oriented along a parallel but separate axis from the first and second dichroic mirrors 414a, 414b such that the third dichroic mirror 414c is offset from the first and second dichroic mirrors 414a, 414b and also centered relative to the first and second dichroic mirrors 414a, 414b. The set of dichroic mirrors 414 are spaced away from each of the LEDs 412 and oriented at an angle α relative to the x-axis. In one example, α may be 45 degrees.

The location and angle of the set of dichroic mirrors 414 relative to the LEDs 412 may be configured to allow a target set of wavelengths to be transmitted to the sample while reflecting shorter wavelengths. Each of the set of dichroic mirrors 414 may be long-pass (LP) dichroic mirror configured with a specific wavelength threshold above which light with sufficiently long wavelengths is able to pass therethrough. The set of dichroic mirrors 414 may therefore be arranged such that each of the set of dichroic mirrors 414 is positioned in a pathway of a suitable LED of the LEDs 412. Light generated at each of the LEDs 412 interacts with at least one of the dichroic mirrors 414 before passing through an output light guide 416.

The transmitted/reflected light (e.g., excitation light) from each of the LEDs 412 may be reflected from the first dichroic mirror 414a, through the output light guide 416 along a linear path 418a parallel with the z-axis, to a first selective mirror 420. A top of the output light guide 416 may be aligned with a top of the emission filter 402 along the x-axis, for example. The first selective mirror 420 may be positioned in the second optical path 346 and oriented at a similar angle with respect to the x-axis as the angle α of the set of dichroic mirrors 414, e.g., 45 degrees.

The excitation light from the LEDs 412 may be reflected at the first selective mirror 420 by 90 degrees, as indicated by arrow 422. The reflected excitation light travels parallel to the x-axis in the second optical path 346 from the first selective mirror 420 to a second selective mirror 424. The first selective mirror 420 may be configured with a coating that causes light of wavelengths below a threshold wavelength to be reflected while light above the threshold wavelength may be transmitted without interference or obstruction through the first selective mirror 420. For example, the threshold wavelength of the first selective mirror 420 may be 700 nm. All excitation light from the LEDs 412 are therefore reflected at the first selective mirror 420 while the laser beam (e.g., the 785 nm red laser) from the LAF sensor 342 passes through the first selective mirror 420, as indicated by arrow 426.

At the second selective mirror 424, the excitation light and a first portion of the laser beam are reflected by 90 degrees, and merge along a common, linear path upwards along the z-axis, as indicated by arrow 428, through the first optical passage 332 to the objective 208. A beam formed of the excitation light and the first portion of the laser beam may continue through the objective to the sample where the excitation light induces fluorescence of the sample. The second selective mirror 424 may be arranged in the first optical passage 332 at the intersection 333 of the first optical passage 332 with the second optical passage 346. The second selective mirror 424 may be oriented at a similar angle relative to the x-axis as the first selective mirror 420, e.g., at the angle α of the set of dichroic mirrors 414. The first portion of the laser beam reflected at the second selective mirror 424 may represent most of the laser beam, e.g., more than 50% of the laser beam photons. The second portion of the laser beam is smaller than the first portion and may be transmitted through the second selective mirror 424 may continue along the x-axis to be attenuated at the housing of the first optical passage 332. The LAF sensor 342 may be preferentially tuned to minimize the second portion of the laser beam.

Upon illumination by the excitation light, the sample may emit light at a different wavelength than a wavelength that induces fluorescence. The emitted light, e.g., emission light, may travel along a linear path from the sample to the camera 338 through the first optical passage 332, as indicated by arrow 430. As such, the second selective mirror 424 is positioned in a path of the emission light and may be configured to allow the emission light to pass therethrough unobstructed. The second selective mirror 424 may thus be adapted with a coating that reflects wavelengths generated by the LEDs 412 and the LAF sensor 342 but transmits expected wavelengths of the emission light. For example, the second selective mirror 424 may allow transmission of wavelengths between 400 and 700 nm. The transmitted light is then filtered as it passes through the emission filter 402, as described above.

The light source 348 may be powered and controlled by a printed circuit board assembly (PCBA). An example of a PCBA 502 is depicted in FIG. 5, which may be coupled to the back side 212 of the blade 202, as shown in FIG. 2. The PCBA 502 is shown without the plate 206 and other components coupled to the plate 206 with the exception of the tube lens 404, the camera mount 408, and the output light guide 416. The PCBA 502 may include various electronic components coupled to a PCB 504. For example, the LEDs 412 of FIG. 4 may be directly coupled to the PCB 504 via soldering. The various electronic components may further include diodes, capacitors, resistors, switches, inductors, etc. The positioning of the PCBA 502 on the back side of the blade 202, opposite of the light source 348, further contributes to maintaining a small footprint of each blade 202 of the multi-detector system 200 of FIG. 2.

A packaging of the components of the quantitative microscopy assembly illustrated in FIGS. 3-5 may provide an optimized balance between suitable distancing between components and minimizing overall dimensions of the blade to accommodate screening of the sample, e.g., distributed in wells of a microplate, above the blades. For example, a distance between a seat of the objective and the tube lens may be no more than 100 mm. An optimal distance between the seat of the objective and the LAF sensor may be 155 mm and an optimal distance between the seat of the objective and the light source may be 190 mm. By utilizing the arrangement of the blade shown in FIGS. 3 and 4, performances of the components may be maintained high without incurring wasted space, e.g., unoccupied and non-useful regions of the blade.

As described above, the vertical stacking of the components of each blade of the multi-detector system 200 of FIG. 2 enables imaging of a microplate arranged above the blades 202. An example of a microplate 600 which may be coupled to a plate holder of the multi-detector system 200 is illustrated in FIG. 6. The microplate 600 has a rectangular outer geometry with a length 604 that is greater than a width 606 of the microplate 600 and includes sidewalls 608 surrounding an array of wells 610. The length 604 and the width 606 of the microplate 600 may conform to specific dimensions according to target specifications, such as ANSI/SLAS specifications. As an example, the length 604 of the microplate 600 may be 127.76 mm and the width 606 of the microplate 600 may be 85.48 mm.

In one example, the microplate 600 may have 96 of the wells 610 distributed evenly (e.g., evenly spaced apart) across the microplate 600. The wells 610 may each have a depth, e.g., along the z-axis, between 10-20 mm and a volume of up to 400 μL, for example, although other depths and volumes are possible. Physical characteristics of the microplate 600 may vary according to a type of applied analysis. For example, when the microplate 600 is used for fluorescence imaging, the microplate 600 may be configured with black walls, e.g., walls of the wells and the sidewalls 608 are black, to reduce background autofluorescence when short half-life fluorophores are used. However, when long half-life fluorophores are used, the walls of the wells 610 and the sidewalls 608 of the microplate 600 may be white to increase fluorescent signals. Floors of the wells 610 may be formed of a clear material to allow imaging of the wells 610 from below the microplate 600.

The microplate 600 may have a foot 612 that forms a base platform of the microplate 600. The foot 612 extends around a perimeter of the microplate 600 at a bottom of the microplate 600 (relative to the z-axis), and extends beyond the sidewalls 608 in the y-x plane. The foot 612 may form a smaller portion of a height 614 of the microplate 600 than the sidewalls 608.

The sidewalls 608 may include at least one chamfer 616. The microplate 600 of FIGS. 6-7 and 9-10 includes two chamfers 616. Other examples of the microplate may include a single chamfer, chamfers at each intersection of the side walls, no chamfers, etc. When the microplate 600 is used to support samples for imaging at the multi-detector system 200, a position of the microplate 600 above the blades 202 of the multi-detector system 200 may be maintained by an assembly configured to contact the microplate 600 and impede undesired movement of the microplate 600.

Figure 7:
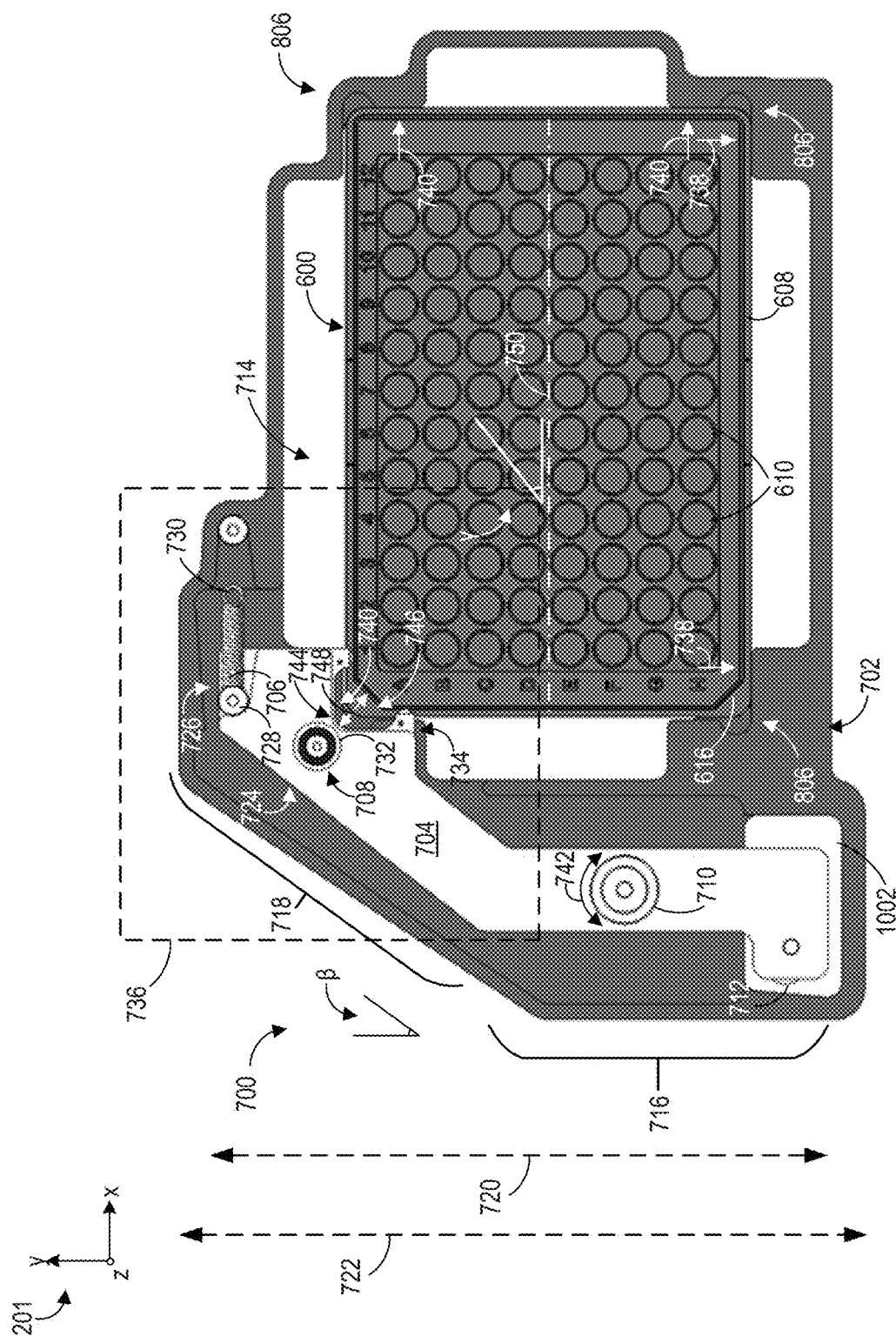
FIG. 7 shows a top view of a plate holder which may be used to secure the microplate of FIG. 6 to the multi-detector quantitative microscopy system.
Figure 8:
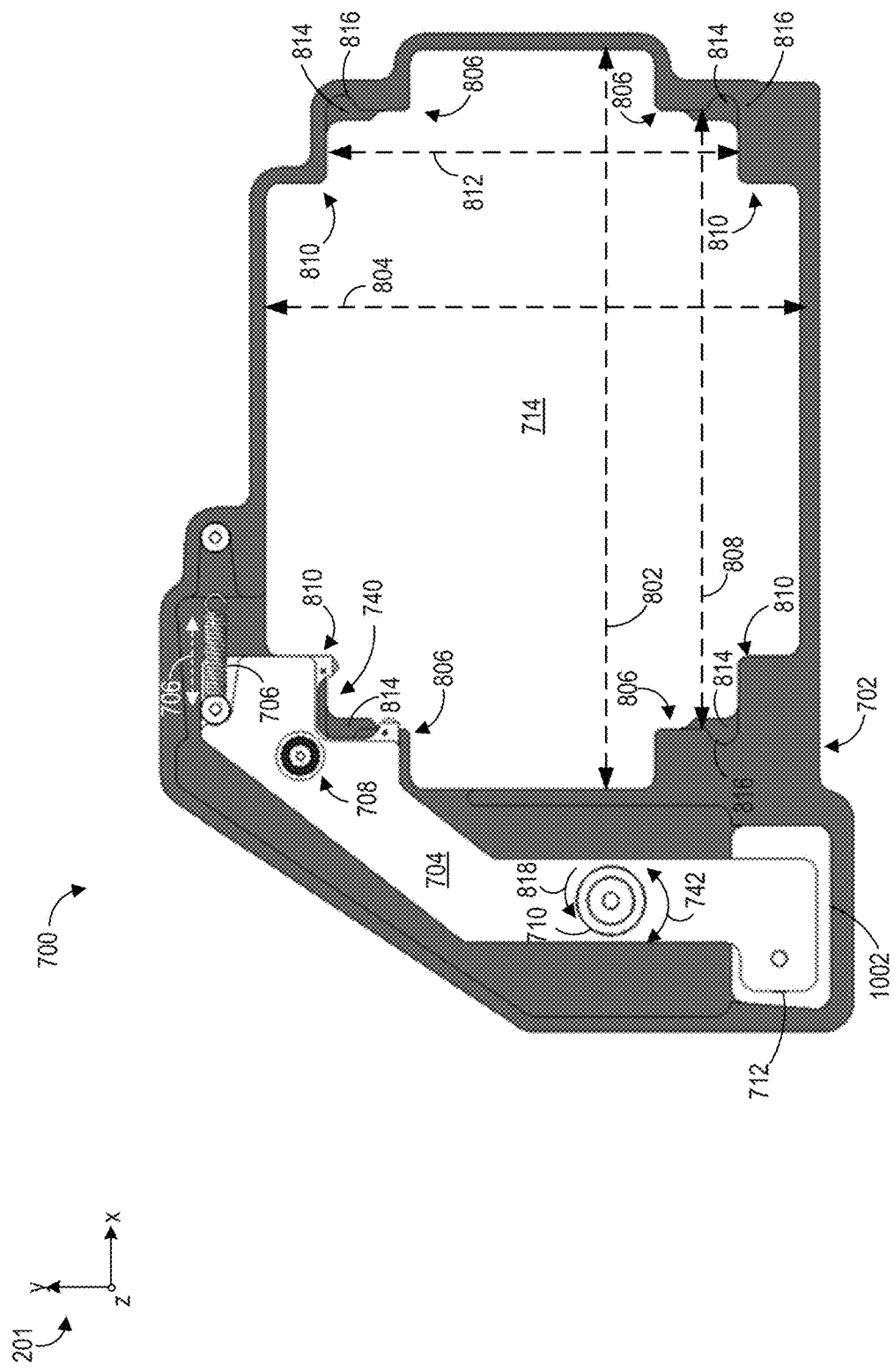
FIG. 8 shows a top view of the plate holder with the microplate removed.
Figure 9:
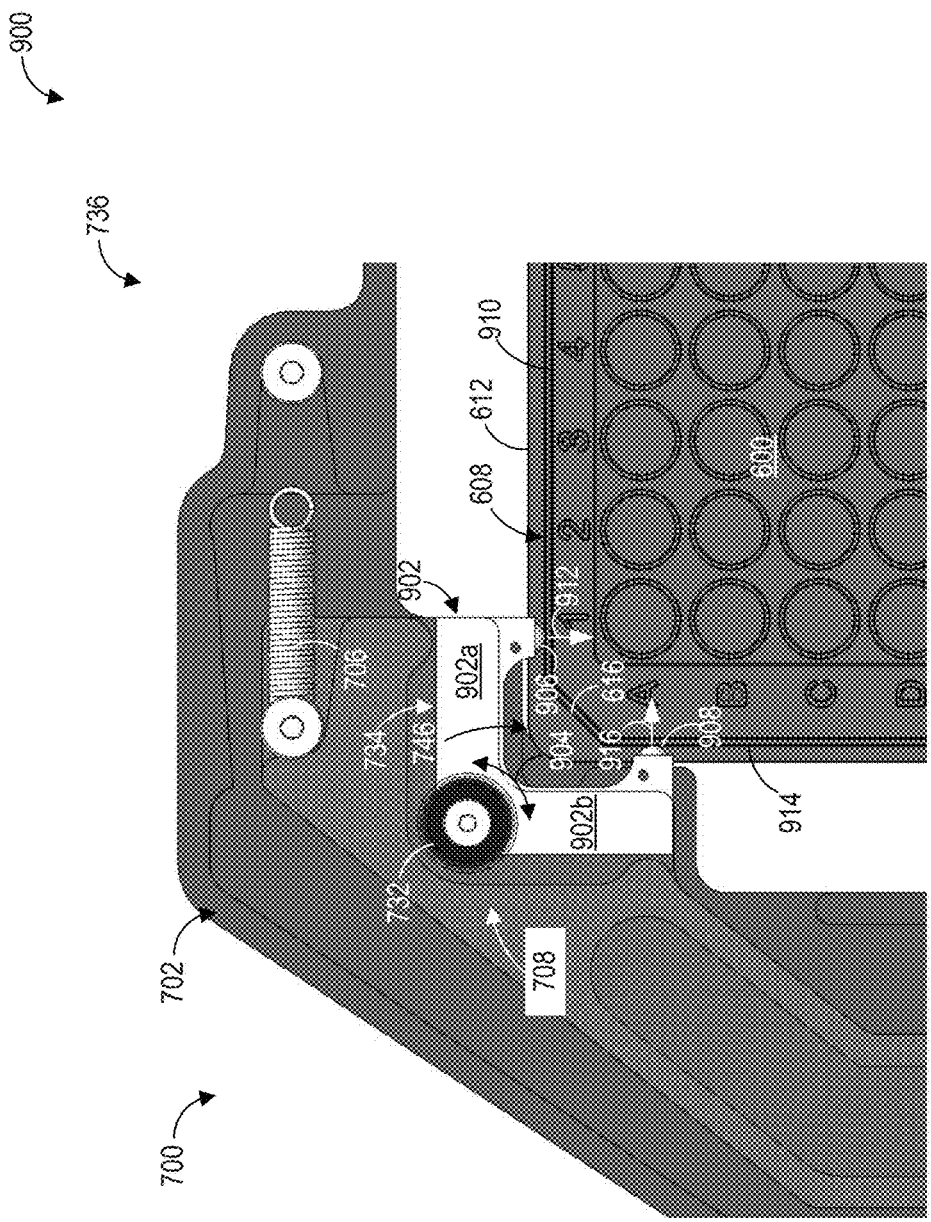
FIG. 9 shows a portion of the plate holder in greater detail.

An example of a plate holder 700 for the multi-detector system 200 is depicted in FIGS. 7-10. The plate holder 700 is illustrated from a top view with the microplate 600 in FIG. 7 and from the top view but without the microplate 600 in FIG. 8. A section of the plate holder 700 is shown in FIG. 9, also from the top view, and the plate holder is depicted from a bottom view in FIG. 10. Turning first to FIG. 7, the plate holder includes a frame 702, a swing arm 704, an extension spring 706, a whippletree assembly 708, a swing arm pivot 710, and a bearing 712.

The frame 702 may have an irregular (e.g., asymmetric along each of the y-z plane and the z-x plane) outer geometry and includes an opening 714. The opening 714 is shown in FIG. 8 without the microplate 600, which may be positioned over the opening 714, illustrating a symmetric shape of the opening 714 across the y-z plane and the z-x plane. A first, maximum length 802 of the opening 714 may be greater than a first, maximum width 804 of the opening 714. Moreover, the first length 802 of the opening 714 may be greater than the length 604 of the microplate 600 (as shown in FIG. 6) and the first width 804 of the opening 714 may be greater the width 606 of the microplate 600 (as shown in FIG. 6).

A portion of the frame 702 surrounding the opening 714 has a first stepped region 806 which may form four corners around a perimeter of the opening 714. The first stepped region 806 may further form a portion of the opening 714 with a second length 808 that is shorter than the first length 802 of the opening 714 and similar to the length 604 of the microplate 600. Additionally, the opening 714 may include a second stepped region 810 also forming four corners around the perimeter of the opening 714, the four corners of the second stepped region 810 offset from the four corners of the first stepped region 806. The second stepped region 810 may form a portion of opening 714 with a second width 812 that is narrower than the first width 804 and similar to the width 606 of the microplate 600.

The opening 714 further includes pads or braces 814 corresponding to corners of the microplate 600 when the microplate 600 is positioned and centered in the opening 714. The braces 814 may be arranged under the microplate 600 to support a vertical position (e.g., with respect to the z-axis) of the microplate 600 and may be in contact with a bottom surface of the microplate 600 at the corners of the foot 612 of the microplate 600 to support a weight of the microplate 600. Vertical surfaces 816 of the frame 702 coupled to the braces 814 may therefore provide guides against which the corners of the microplate 600 may abut. When the microplate 600 is placed in the opening 714, the microplate 600 is supported by the frame 702 with gaps in the frame extending along each side of the microplate 600, as shown in FIG. 7. The gaps may be sufficiently large to allow a user's fingers to inserted therethrough, allowing the microplate 600 to be easily placed onto the plate holder 700 without unintentional bumping of user's fingers against the frame 702.

The swing arm 704 may extend along a portion of the frame 702 adjacent to the opening 714. For example, as shown in FIGS. 7-10, the swing arm 704 may be located to the left of the opening in the plate holder 700. A length 720 of the swing arm may be greater than the width 606 of the microplate 600 but shorter than a maximum width 722 of the frame 702. As shown in FIG. 7, the swing arm 704 may include a first portion 716 and a second portion 718 which may be continuous with one another. The first portion 716 may extend along the frame 702 linearly and parallel with the y-axis. The second portion 718 may also extend linearly along the frame 702 but at an angle β relative to the y-axis. In one example, the angle β may be 45 degrees. In other examples, however, the angle β may be an angle between 30 to 60 degrees.

The angled extension of the second portion 718 of the swing arm 704 allows a head 724 of the swing arm 704 to be positioned adjacent to the microplate 600 at a top left-hand corner of the microplate 600, with respect to the top view depicted in FIGS. 7-9. The head 724 includes a 90-degree cutout 744 to accommodate both an arrangement of the whippletree assembly 708 thereat and a protrusion of a first corner 746 of the microplate 600 into the head 724 of the swing arm 704. The 90-degree cutout 744 is located along an edge of the swing arm 704 proximate to the microplate 600. The extension spring 706 may be coupled to a first end 726 of the swing arm 704, the first end 726 included in the head 724 of the swing arm 704. The extension spring 706 may be attached at one end to the swing arm 704 by a first fastener 728, such as a bolt, and attached at an opposite end to the frame 702 by a similar second fastener 730.

The extension spring 706 may extend between the first and second fasteners 728, 730 parallel with the x-axis and is depicted in a first, stretched position in FIGS. 7 and 8. In other words, the extension spring 706 may be under tension due to a stiffness of the extension spring 706 that resists stretching. For example, the extension spring 706 may be configured with a high stiffness, e.g., a high resistance to elongation of the extension spring 706. As an example, the extension spring 706 may have a spring force of 1.3-2.3 pounds.

The whippletree assembly 708 may be positioned at the head 724 of the swing arm 704 and aligned with a diagonal axis of the microplate 600. The whippletree assembly 708 may include a pivot 732 and a yoke 734 which may be illustrated with greater clarity in an expanded view 900 of a section of the plate holder 700 indicated by dashed area 736 and shown in FIG. 9. The expanded view 900 of FIG. 9 shows the whippletree assembly 708 with the swing arm 704 omitted.

The yoke 734 may be a bracket with two arms 902 oriented perpendicular to one another, including a first arm 902a extending parallel with the x-axis and a second arm 902b extending parallel with the y-axis. The yoke 734 is coupled to the frame 702 of the plate holder 700 at an intersection of the arms 902 by the pivot 732. In addition to securing the yoke 734 to the frame 702, the pivot 732 may also control a degree to which the yoke 734 may rotate around the pivot 732, as indicated by arrow 904.

For example, the pivot 732 may include a spring mechanism that constrains rotation of the yoke 734 in either a clockwise or counter-clockwise direction to a threshold degree of rotation. In one example, the threshold degree of rotation may be 10 degrees in either direction relative to the position of the yoke 734 shown in FIG. 9. In other examples, the yoke 734 may pivot 1.25 degrees in either direction relative to the position of the yoke 734 shown in FIG. 9. In one example, the spring mechanism of the pivot 732 is excluded and the threshold degree of rotation (e.g., pivoting of the yoke 734 1.25 degrees in either direction) is established by hard stops in a range of rotation of the yoke 732 established by geometry of the yoke 732. The yoke 732 may pivot within the range of rotation. Resistance of the pivot 732 to rotation of the yoke 734 beyond the threshold degree of rotation may be equal in both directions. Furthermore, in examples including the spring mechanism, the yoke 734 may be maintained oriented such that the first arm 902a remains parallel with the x-axis and the second arm 902b remains parallel with the y-axis regardless of a position of the swing arm 704.

A pressure exerted on the microplate 600 by the whippletree assembly 708 may be evenly distributed between the arms 902 of the yoke 734 based on a combination of an angle of the swing arm 704 relative to the microplate 600 and transmission of the stiffness of the extension spring 706 to the microplate 600 as a compressive force. The arms 902 may exert pressure on the microplate 600 due to tension at the extension spring 706 (described further below) via a first contact ball 906 coupled to an end of the first arm 902a and a second contact ball 908 coupled to an end of the second arm 902b.

The swing arm 704 may be configured to rotate about the swing arm pivot 710 (described further below in detail) such that the head 724 swings toward and away from the microplate 600, as indicated by arrow 748, at an angle γ relative to a longitudinal axis 750 of the microplate 600, as shown in FIG. 7. In one example, the angle γ is 45 degrees which allows the first and second contact balls 906, 908 to contact the microplate 600 at the same time when the head 724 of the swing arm 704 travels toward the microplate 600. The first and second contact balls 906, 908 may be interfaces between the whippletree assembly 708 and the microplate 600 and may press against the microplate 600 in perpendicular directions. The contact balls may be formed of a rigid material, such as stainless steel or aluminum. As another example, the contact balls may be formed of a more flexible material, such as rubber.

For example, when the whippletree assembly 708 presses against the microplate, the first arm 902a of the yoke 734 may exert a force against a first section 910 of the sidewalls 608 of the microplate 600. The force is transmitted through the first contact ball 906, as indicated by arrow 912. The second arm 902b of the yoke 734 may exert a force against a second section 914, the second section 914 perpendicular to the first section 910, of the sidewalls 608 of the microplate 600. The force is transmitted through the second contact ball 908 as indicated by arrow 916 and may be equal to the force transmitted through the first contact ball 906. In this way, the forces applied to sidewalls 608 of the microplate 600 from the whippletree assembly 708 are distributed evenly between the first contact ball 906 and the second contact ball 908 in two directions normal to one another, thereby stabilizing the position of the microplate 600 in the opening 714 of the frame 702. For example, as shown in FIG. 9, the first arm 902a of the yoke 734 may press the microplate 600 against the first stepped region 806 as indicated by arrows 738 and the second arm 902b of the yoke 734 may press the microplate 600 against the first stepped region 806 as indicated by arrows 740.

By transmitting the force applied by the whippletree assembly 708 to the microplate 600 through the first and second contact balls 906, 908, the force is directed through a single, concentrated point where each of the first and the second contact balls 906, 908 directly contact the sidewalls 608 of the microplate 600, at points beyond, e.g., further along the length 604 and the width 606 of the microplate 600 (as shown in FIG. 6), the chamfer 616 at the first corner 746. Application of the force through the single, concentrated points of contact circumvents transmission of torque from the yoke 734, when the yoke 734 rotates about the pivot 732. In other words, regardless of how the yoke 734 is oriented relative to the pivot 732, the forces applied to the microplate 600 from the yoke 734 remains evenly balanced between the first and second contact balls 906, 908 such that the microplate 600 is pressed against the frame 702 with a same compressive force in the direction indicated by arrows 738 as in the direction indicated by arrows 740, as shown in FIG. 7.

In addition, by separating the points of contact between the whippletree assembly 708 and the microplate 600, e.g., at the contact balls, the whippletree assembly 708 may accommodate variations in microplate width and length. Furthermore, an ability of the whippletree assembly 708 to clamp the microplate 600 in place is unchanged whether or not the first corner 746 of the microplate 600 includes the chamfer 616.

As shown in FIGS. 7 and 8, the first portion 716 of the swing arm 704 includes the swing arm pivot 710. The swing arm pivot 710 may be a fulcrum about which the swing arm 704 may rotate, as indicated by arrow 742 in FIG. 7. In addition, the swing arm 704 may be connected to the frame 702 of the plate holder 700 by the swing arm pivot 710. In one example, the swing arm pivot 710 may be a bearing configured to allow pivoting of the swing arm 704 in either of a clockwise or counter-clockwise direction. An amount of rotation of the swing arm 704 in either direction may be constrained by the extension spring 706.

For example, as shown in FIG. 8 and indicated by arrow 818, when the swing arm 704 rotates in the counter-clockwise direction (with respect to the top view of the plate holder 700 shown in FIG. 8), the rotation is resisted by increased stretching of the extension spring 706 to a second position. The resistance of the extension spring 706 to the counter-clockwise rotation may increase as the swing arm 704 continues pivoting, which results in the head 724 of the swing arm 704 moving away from the opening 714 of the frame 702, until the extension spring 706 reaches a maximum stretching tolerance. When the extension spring is in the second position, the contact balls of the yoke 734 are no longer in contact with the microplate 600. Tension on the extension spring 706 increases as the head 724 swings farther away from the opening 714 of the frame (as well as from the first corner 746 of the microplate 600 when the microplate 600 is positioned in the frame 702). As such, the swing arm 704 may rotate in the counter-clockwise direction to a maximum of five degrees in both directions of the orientation shown in FIG. 8 without causing deformation of the extension spring 706.

Rotation of the swing arm 704 in the clockwise direction from the position of the swing arm shown in FIGS. 7-10 may be experience less resistance due to release of tension on the extension spring 706, e.g., extension spring 706 becomes less tense, allowing the length of the extension spring 706 to decrease. When the extension spring 706 reaches the first position, as shown in FIGS. 7 and 8, the contact balls of the yoke 734 may press against the microplate 600 according to the stiffness of the extension spring 706.

The spring force or stiffness of the extension spring 706, as well as a length of the extension spring (the length defined along the x-axis), may be configured to provide a suitable amount of tension when the first and second contact balls 906, 908 of the whippletree assembly 708 are in contact with the microplate 600 when the microplate 600 is positioned in the opening 714 of the frame 702 as shown in FIG. 7. When the microplate 600 is not present, the extension spring 706 may be in a third position where the extension spring 706 is at a minimum length and less stretched than in the first or second positions. The extension spring 706 may be further stretched, such as 5-10% longer when the contact balls engage with the microplate 600 compared to when the microplate 600 is not present. Thus the counteracting stiffness of the extension spring 706 (e.g., resistance to stretching) may exert a suitable amount of compression on the microplate 600, as transmitted through the contact balls, to hold the microplate 600 securely within the opening 714 of the frame 702.

To release the microplate 600 from the force exerted by swing arm 704, the swing arm 704 may be pivoted about the swing arm pivot 710 in the counter-clockwise direction until the force from the swing arm 704 is alleviated. In some examples, the swing arm 704 may be rotated until the contact balls are no longer in contact with the microplate 600. Rotation of the swing arm 704 may be facilitated by adjustment of a position of the bearing 712.

Figure 10:
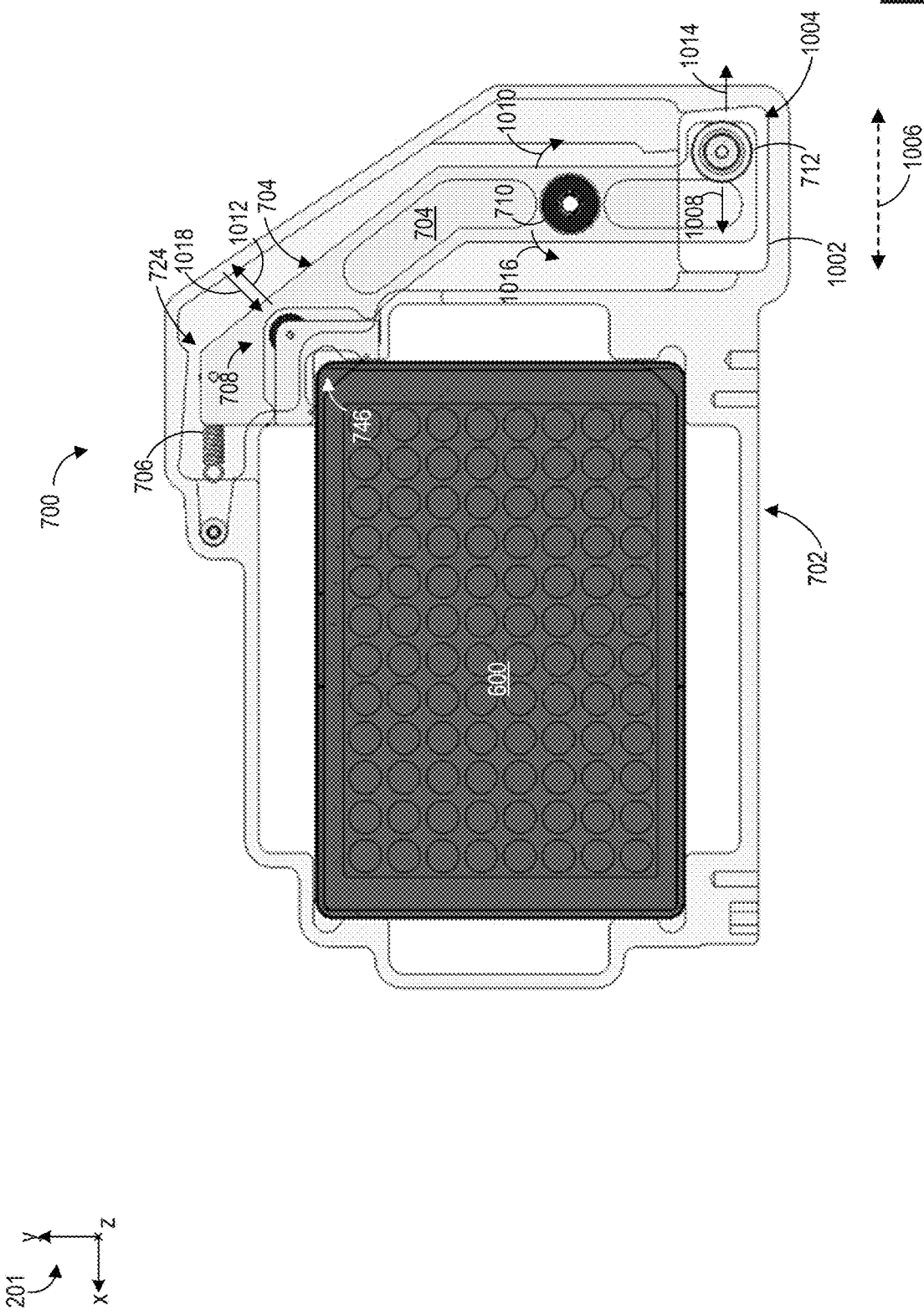
FIG. 10 shows a bottom view of the plate holder.

For example, as shown in FIG. 10 in a bottom view of the plate holder 700 with the frame 702 depicted as transparent for clarity, at least a portion of the bearing 712 is located under the frame 702. In other words, the bearing 712 may extend through a window 1002 of the frame 702 with the portion of the bearing located under the frame 702 arranged on an opposite side of the frame 702 from the swing arm 704. The bearing 712 may be coupled to the swing arm 704 through a window 1002 of the frame 702. In one example, the bearing 712 may be fixedly coupled to a tail end 1004 of the swing arm 704.

The window 1002 is located directly below the tail end 1004 of the swing arm 704 and may have a greater width 1006 than a width of the swing arm 704 at the tail end 1004. When the bearing 712 is shifted to the left, as indicated by arrow 1008, the swing arm 704 rotates about the swing arm pivot 710 as indicated by arrow 1010. As the swing arm 704 rotates as indicated by arrow 1010, the head 724 swings away from the first corner 746 of the microplate 600, as indicated by arrow 1012, against the spring force of the extension spring 706. As described above with reference to FIG. 7, the head 724 travels at the angle γ relative to the longitudinal axis 750 of the microplate 600. The forces exerted by the first and the second contact balls 906, 908 of the whippletree assembly 708 are removed from the microplate 600 at the same time when the head 724 moves away from the microplate 600. Movement of the bearing 712 may be halted when the contact balls are no longer in contact with the microplate 600.

When the contact balls of the whippletree assembly 708 are no longer in contact with the microplate 600, the microplate 600 may be removed, replaced, or added to the plate holder 700 without interference from the swing arm 704. To engage the swing arm 704 with the microplate 600, e.g., upon replacement or installation of the microplate 600 in the plate holder 700, the bearing 712 may be displaced, e.g., shifted, as indicated by arrow 1014, causing the swing arm 704 to pivot about the swing arm pivot 710 as indicated by arrow 1016. The head 724 of the swing arm 704 moves towards the first corner 746 of the microplate 600, as indicated by arrow 1018, until the contact balls come into contact with the microplate 600, at which movement of the bearing 712 is halted. As described above, the extension spring 706 may remain under tension to clamp the microplate 600 within the opening 714 of the frame 702.

Figure 11A:
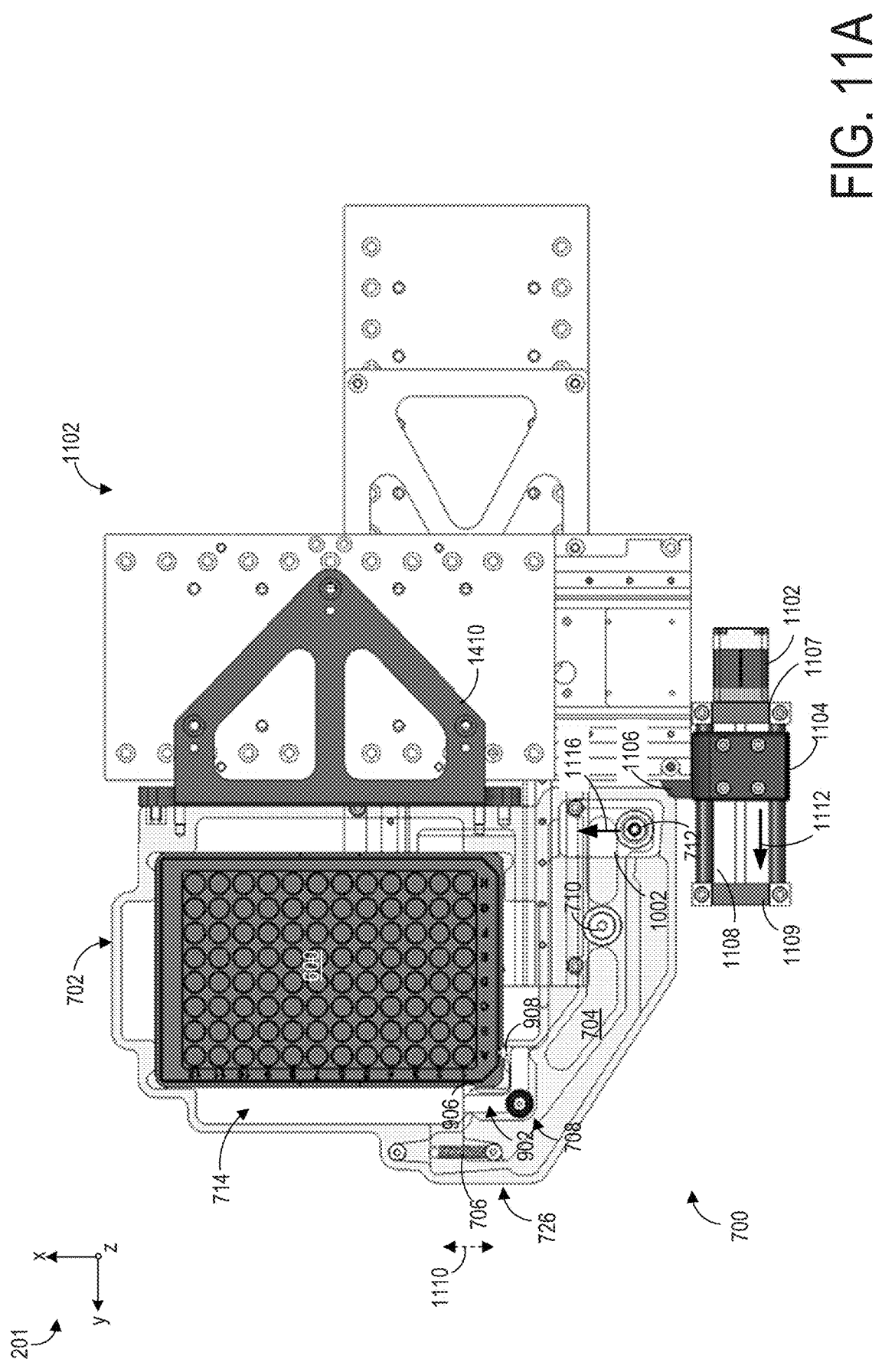
Figure 11B:
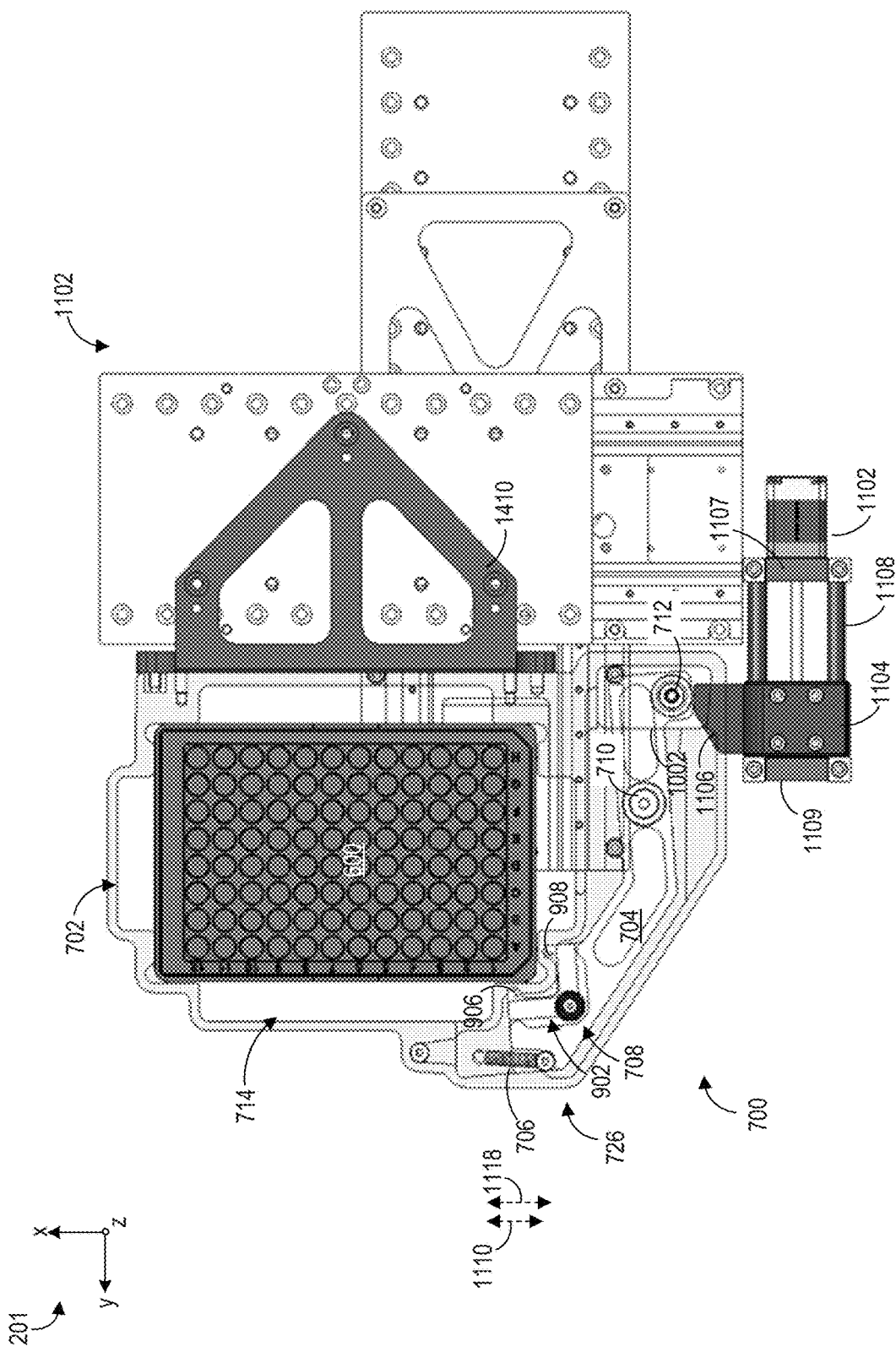
FIG. 11B. shows a view of the plate holder with the mechanism for moving the plate holder in a second position.

In one example, displacement of the bearing 712 may be controlled by an actuating system for the swing arm 704, including a motor 1102, a ram 1104 with a ramped surface 1106, as shown in FIGS. 11A-11B in a top view of the plate holder 700. It will be noted that the top view of FIGS. 11A-11B is rotated by 90 degrees relative to the views of FIG. 7-9. The plate holder 700 is depicted coupled to a stage 1150 which adjusts a position of the plate holder 700 along the x-y plane relative to the multi-detector system 200. The swing arm 704 is engaged with the microplate 600 in FIG. 11A and disengaged from the microplate 600 in FIG. 11B.

The motor 1102 may be connected to the ram 1104, where the ram 1104 includes the ramped surface 1106 protruding upwards (along the x-axis) from the ram 1104, and the ram 1104 may be configured to slide along a set of rods 1108, e.g., along the y-axis. The motor 1102 may be arranged below a plane of the swing arm 704 (e.g., a y-x plane) and actuation of the motor 1102 may compel movement of the ram 1104 along the set of rods 1108 which may control engagement of the swing arm 704 with the microplate 600 via the position of the bearing 712, as described above. For example, when the swing arm 704 is engaged with the microplate 600, as shown in FIG. 11A, the bearing 712 is in a first position along the x-axis and the extension spring 706 is stretched to a first length 1110, corresponding to the first position of the extension spring 706. When stretched to the first length 1110, a corresponding amount of tension at the extension spring 706 causes the first end 726 of the swing arm 704 to apply a sufficient amount of compression, via the first and second contact balls 906, 908, to clamp the microplate 600 in place within the opening 714 of the frame 702 during translation of the plate holder 700 by the stage 1150.

Furthermore, when the swing arm 704 is engaged, the ram 1104 is retracted to the right along the set of rods 1108, e.g., to a retracted position. In the retracted position, the ram 1104 is positioned as close to the motor 1102 as allowable by a first cross-beam 1107 coupling the set of rods 1108 to one another. When the ram 1104 abuts the first cross-beam 1107, the ramped surface 1106 of the ram 1104 may be spaced away from the bearing 712 by a maximum distance. When the motor 1102 is actuated to disengage the swing arm 704, the motor 1102 may drive sliding of the ram 1104 to the left, as indicated by arrow 1112 in FIG. 11A. As the ram 1104 slides to the left, a distance between the ramped surface 1106 and the bearing 712 decreases until the ramped surface 1106 comes into contact with the bearing 712. Continued movement of the ram 1104 to the left with the ramped surface 1106 in contact with the bearing 712 forces the bearing 712 to slide along the ramped surface 1106. For example, the bearing 712 may move upwards, with respect to the x-axis, as indicated by arrow 1116.

The motor 1102 may continue propelling the ram 1104, against the stiffness of the extension spring 706, to the left until the ram 1104 abuts a second cross-beam 1109 coupling the set of rods 1108 to one another, as shown in FIG. 11B. The ram 1104 is shifted to a fully extended position in FIG. 11B and the displacement of the bearing 712 upwards, along the x-axis causes the first end 726 of the swing arm 704 to swing away from the microplate 600. The first and second contact balls 906, 908 are no longer in contact with the microplate 600. The extension spring 706 is stretched further to a second length 1118 that is greater than the first length 1110, thereby increasing tension at the extension spring 706.

When the ram 1104 is in the fully extended position of FIG. 11B, the microplate 600 may be loaded, removed or replaced. In some examples, loading/removal/replacement may be performed manually, e.g., by a user, and in other examples, the loading/removal/replacement may be achieved by an automated system such as a robotic arm.

It will be appreciated that the actuating system for engaging/disengaging the swing arm 704 described above is a non-limiting example and other mechanisms have been contemplated. For example, an alternate mechanism may include using a non-moving surface and driving the bearing 712 to and from the non-moving surface using an actuation system of the stage 1150.

The microplate 600 may allow a large number of samples to be screened concurrently. By positioning the microplate 600 above the multi-detector system 200, the blades 202 may synchronously capture imaging data from portions of the microplate 600 to generate a complete image of the microplate 600.

The blades 202 of the multi-detector system 200 may be configured as shown in FIGS. 3-5 to enable the x-shaped assembly of the multi-detector system 200. The x-shaped configuration allows the objectives 208 of each blade 202 to be positioned relative to one another with optimized spacing in between. For example, as shown in FIG. 12, the blades 202 include (along a clockwise direction) a first blade 202a with a first objective 208a, a second blade 202b with a second objective 208b, a third blade 202c with a third objective 208c, and a fourth blade 202d with a fourth objective 208d. The blades 202 are oriented such that the objective 208 are proximate to a center of the x-shaped configuration and the LAF sensor 342 of each blade 202 is positioned at outer regions of the x-shaped configuration.

Along a first axis 1202, the first axis 1202 parallel with the y-axis, the first objective 208a is spaced away from the second objective 208b by a first distance 1204. The third objective 208c is also spaced away from the fourth objective 208d by the first distance 1204 along the first axis 1202. Along a second axis 1206, the second axis 1206 parallel with the x-axis, the first objective 208a is spaced away from the fourth objective 208d by a second distance 1208. The second objective 208b is also spaced away from the third objective 208c by the second distance 1208 along the second axis 1206.

The second distance 1208 is greater than the first distance 1204. In one example, the first distance may be 2.25 mm and the second distance 1208 may be 20.57 m. The differences in the distances may result in greater overlap between FOVs of the objectives along the first axis 1202 than the second axis 1206. For example, the FOV of the first objective 208a may overlap to a greater extent with the FOV of the second objective 208b than the fourth objective 208d. Furthermore, the FOV of the first objective may overlap to a greater extent with the FOV of the fourth objective 208d than with the FOV of the third objective 208c.

By incorporating a greater distance between the objectives 208 along the second axis 1206 than along the first axis 1202, an overall, combined FOV of the objectives 208 may be larger along the second axis 1206 than along the first axis 1202. For example, a first FOV of the first objective 208a is indicated by dashed circle 1210, a second FOV of the second objective 208b is indicated by dashed circle 1212, a third FOV of the third objective 208c is indicated by dashed circle 1214, and a fourth FOV of the fourth objective 208d is indicated by dashed circle 1216. A combined, overall FOV resulting from an overlap between the FOVs of the objectives 208 has a width 1218 along the first axis 1202 and a length 1220 along the second axis 1206.

Due to the different spacing between the objectives 208 along the first axis 1202 versus the second axis 1206, the length 1220 is greater than the width 1218 of the overall FOV. As such, dimensions of the overall FOV accommodates the rectangular geometry of the microplate, e.g., the microplate 600 of FIGS. 6-7 and 9-10, as indicated by dashed rectangle 1222. By spacing the objectives 208 apart by a greater distance along the length of microplate (e.g., along the x-axis), than the width of the microplate (e.g., along the y-axis), a complete image capturing each well of the microplate may be obtained.

Furthermore, the spacing between the objectives 208, e.g., where the spacing is greater along the second axis 1206 than the first axis 1202 where both the axes are horizontal axes arranged normal to one another, may enable efficient, high speed imaging of the microplate, e.g., the microplate 600 of FIGS. 6-, 7, and 9-11B. An arrangement of the objective 208 results in a radial distribution of the objective FOVs, each configured with similarly large FOVs, such that each objective captures a portion of the microplate with each imaging event and a focus of the objectives does not stray beyond, e.g., outside of, the imaging area of the microplate, even when the microplate position is adjusted. An overall rectangular orientation of the objectives 208 enables complete imaging of the entire microplate simultaneously. Imaging of the microplate may be repeatedly cycled at a high rate as a result.

Returning to FIG. 2, the blades 202 of the multi-detector system 200 may be coupled to an isolated base 222 of the housing 220, and may extend upwards from the isolated base 222. The isolated base 222 may be a rigid, solid plate and may include various apertures to allow fastening devices to be inserted therethrough. Each of the blades 202 may be attached to the isolated base 222 by brackets 224 and fasteners 226. The isolated base 222 may have a substantially square geometry and the blades 202 may be oriented along the isolated base 222 such that the width (e.g., the width 314 of FIG. 3) of each blade is aligned with a diagonal axis across the isolated base 222 (e.g., an axis extending across opposite corners of the isolated base 222). As shown in FIG. 2 and FIG. 12, the blades 202 do not contact one another.

The multi-detector system 200 is depicted in FIGS. 13 and 14, from a front view and a perspective view, respectively, with the blades 202 enclosed by the complete housing 220 (e.g., FIG. 2 shows only portions of the housing 220). As such, the housing 220 also includes a top plate 1302 coupled to top edges of two oppositely arranged side walls 1304. The top plate 1302 may be a rigid plate with a square geometry and may have similar dimensions to the isolated base 222. As shown in FIG. 13, a bottom face 1306 of the top plate 1302 may be in contact with the top edge 326 of the plate 206 of each blade 202. The objective 208 of each blade 202 may protrude above a top surface 1308 of the top plate 1302, between the top surface 1308 and the plate holder 700, when the plate holder 700 is positioned over the objectives 208. As shown in FIG. 14, the stage 1150, configured to adjust the position of the plate holder 700 along the top plate 1302, is coupled to the plate holder 700.

As depicted in FIG. 13, the objectives 208 extend upwards from the blades 202 into a space between the top plate 1302 and the plate holder 700 but does not contact the plate holder 700 or the microplate (e.g., the microplate 600 of FIGS. 6-7 and 9-10) supported by the plate holder. The plate holder 700 may be translated along the x-y plane without obstacles impeding movement of the plate holder 700. A distance that the plate holder 700 is vertically spaced away from the objectives 208 may be configured to allow the objectives 208 to be positioned at a target distance from the microplate 600, located above, and a target distance from the tube lenses (e.g., the tube lens 404 of FIG. 4), located below. By placing the objectives 208 at the target distances from the microplate 600 and the tube lenses, a maximum FOV and resolution may be obtained from the quantitative microscopy assemblies of the multi-detector system 200.

The plate holder 700 may be coupled to the stage 1150, the stage 1150 also positioned above the top plate 1302 of the housing 220 and attached to the top plate 1302. As shown in FIGS. 11A, 11B and 14, the plate holder 700 may include a portion that extends onto and over the stage 1150, forming a bracket 1410. As shown in FIG. 14, the bracket 1410 may be secured to the stage 1150 via fasteners, thereby fixedly coupling the stage 1150 to the plate holder 700. The stage 1150 is arranged alongside the plate holder 700 (with the exception of the bracket 1410 of the plate holder 700) such that the stage 1150 is located beside the microplate 600 when the microplate 600 is positioned in the opening (e.g., the opening 714 of FIG. 8) of the plate holder 700.

The stage 1150 may be a two-axis stage configured with bearings, such as mechanical bearings, air bearings, etc., to allow the plate holder 700 to translate along each of the x-axis and the y-axis relative to the objectives 208. In some examples, movement of the stage, and therefore of the plate holder 700, may be controlled by a motor. In other examples, a relative position of the stage 1150 may be manually adjusted. Adjustment of the positioning of the stage 1150 allows the FOVs of the objective 208 to be modified with respect to the microplate 600, allowing complete imaging of the microplate 600.

The side walls 1304 of the housing 220 extend between the top plate 1302 and the isolated base 222 on opposite sides of the top plate 1302 and the isolated base 222. The side walls 1304 may be similarly configured to one another and, as shown in FIG. 2, may include openings 228 to allow the blades 202 to be easily accessed through the openings 228. As illustrated in FIG. 14, the openings 228 may be hidden by removable covers 1402 to block undesired entry of external objects through the openings 228. A height 1305 (indicated in FIG. 13) of the side walls 1304 may be similar to the height 312 of the blades 202, as shown in FIG. 3, to enable protrusion of the objectives 208 above the top plate 1302 of the housing 220.

As shown in FIG. 13, the blades 202 may be spaced away from the side walls 1304 so that the blades 202 do not contact the side walls 1304. Each of the blades 202 may be oriented similarly around the central axis 204 such that the front side 210 of one the blades 202 faces the back side 212 of the blade in front and the back side of the blade faces the front side 210 of the blade behind. Furthermore, the blades 202 are oriented with the inner side 302 of each blade proximate to the central axis 204. As such, the objectives 208 of the blades 202 are clustered around the central axis 204 at an upper region of the multi-detector system 200 and spaced apart as described above with reference to FIG. 12.

The orientation of the blades 202 also positions the notched section 316 of the inner side 302 of each of the blades proximate to the central axis 204. As illustrated in FIG. 14, clustering of the notched section 316 of each blade 202 around the central axis 204 forms an area of space in which a central fan 1404 may be located. The multi-detector system 200 is shown resting on a chassis 1406 in FIG. 14, the chassis 1406 including a bottom plate 1408. The chassis 1406 may support peripheral components such as electronic devices coupled to the multi-detector system 200.

As shown in FIG. 15, the central fan 1404 may be coupled to the bottom plate 1408 of the chassis 1406 and extend upwards, along the z-axis from the bottom plate 1408, through an opening 1601 in the isolated base 222 of the housing 220, the opening 1601 illustrated in FIG. 16. The opening 1601 in the isolated base 222 may be sized such that edges of the opening do not contact the central fan 1404. Vibrations from the central fan 1404 are therefore not propagated through the housing 220 and blades 202 of the multi-detector system 200. As shown in FIG. 15, the central fan 1404 has a lower portion 1502, the lower portion 1502 extending between the bottom plate 1408 and the isolated base 222, and an upper portion 1504, the upper portion 1504 protruding above the isolated base 222. The lower portion 1502 of the central fan 1404 may be a cylindrical duct with a plurality of slots 1506. The plurality of slots 1506 may fluidically couple air outside of the lower portion 1502 of the central fan 1404 to air inside of the lower portion 1502 of the central fan 1404.

The upper portion 1504 includes a mount 1508 and an impeller 1602, as shown in FIG. 16 in a top view of the central fan 1404. The mount 1508 may have a square outer geometry and may include vertical walls, as shown in FIGS. 14 and 15, that surround the impeller 1602 and fasteners 1604 that secure the mount 1508 to the isolated base 222. A hub 1606 of the impeller 1602 may be rotatably coupled to the mount 1508. A motor driving rotation of the impeller 1602 may be arranged below the hub 1606, under the isolated base 222 and enclosed by the lower portion 1502 of the central fan 1404.

When the central fan 1404 is actuated, e.g., by operation of the motor, rotation of the impeller 1602 draws air laterally into the lower portion 1502 of the central fan 1404 from a space between the isolated base 222 and the bottom plate 1408 of the chassis 1406, as indicated in FIG. 15 by arrows 1510. The air is pulled into the lower portion 1502 through the plurality of slots 1506 and pushed upwards, along the central axis 204, driving air flow across surfaces of the blades 202, as indicated by arrows 1512.

As the air flow upwards, heat is extracted from components of the blades 202 arranged along the inner side 302, such as the emission filter 402 and the tube lens 404 depicted in FIG. 4. The air may also cool the camera mount 408. By arranging the central fan 1404 at a central region of the isolating base 222 of the multi-detector system 200, enhanced thermal management of heat-generating and heat-sensitive components is enabled. The multi-detector assembly may further include a conventional cooling system, such as a fan mounted along a rear wall of an outer casing of the multi-detector system 200 (not shown).

As shown in FIGS. 2, 13, and 14, the housing 220 of the multi-detector system 200 may also include vibration isolators 230 coupled to the isolated base 222 of the housing 220 and interfacing with the bottom plate 1408 of the chassis 1406. The vibration isolators 230 may be supports upon which the housing 220 of the multi-detector system 200 sits. The vibration isolators 230 may have L-shaped profiles with a planar base 232, or foot 232, that directly contacts the bottom plate 1408 of the chassis 1406 of FIG. 14. Vertical portions 234 (e.g., aligned with the z-axis) of the vibration isolators 230 may extend through a corresponding opening in the isolated base 222 and may be fitted with a fastener to secure the vibration isolators 230 to the isolated base 222.

The multi-detector system 200 is depicted with three vibration isolators 230 herein but may include more of the vibration isolators 230 in other examples. As shown in FIGS. 2 and 14, two of the vibration isolators 230 are positioned proximate to a first edge 236 of the isolated base 222 and aligned with one another along the first edge 236. The two vibration isolators 230 are spaced apart from one another such that each of the vibrations isolators 230 is proximate to one of the side walls 1304. The feet 232 of the two vibration isolators 230 may be oriented such that a length of the feet 232 (e.g., a longest dimension of the feet 232) is parallel with the y-axis and extending from the vertical portions 234 in a direction away from the blades 202.

As shown in FIG. 13, a third of the vibration isolators 230 (e.g., a third vibration isolator 231) may be positioned along a second edge 1310 of the isolated base 222, opposite of the first edge 236. The third vibration isolator 231 may be located in a central region along the second edge 1310 of the isolated base 222, as illustrated in FIG. 13. The foot 232 of the third vibration isolator 231 may be oriented perpendicular relative to the feet 232 of the two vibration isolators 230 positioned along the first edge 236 of the isolated base 222, with a length of the foot 232 of the third vibration isolator 231 parallel with the x-axis.

At least a portion of the vibration isolators 230 may be formed of a flexible, dampening material, such as rubber. Vibrational motion generated at the electronic components supported by the chassis 1406, as shown in FIG. 14, and transmitted through the chassis 1406 may therefore be absorbed by the vibration isolators 230. The housing 220 and the blades 202 of the multi-detector system 200 are thereby isolated from the vibrational motion, thus reducing noise in the imaging data. The positioning of the vibration isolators 230 along the isolated base 222 and the orientation of the feet 232 provide stability to the housing 220 such that the multi-detector system 200 remains level and resistant to tipping while minimizing points of contact between the bottom plate 1408 of the chassis 1406 and the isolated base 222 through which oscillating motions may be transmitted.

Imaging of the microplate by the multi-detector assembly may rely upon an ability of each quantitative microscopy assembly to rapidly focus on a suitable focal point along a depth of the microplate, e.g., with respect to the z-axis. However, a presence of multiple interfaces between samples, located in the wells of the microplate, and the objectives may confound a process for selecting a correct interface for obtaining high resolution images of the samples. To address this issue, a process for adjusting the focus of each objective of the multi-detector assembly may be implemented at a controller of the multi-detector assembly, such as the controller 124 of FIG. 1. The process is described below with reference to FIGS. 17-24.

Figure 17:
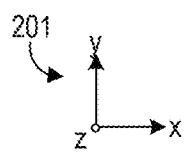
FIG. 17 shows an example of a field of view of an objective of the multi-detector quantitative microscopy system overlaid with a grid.
Figure 17:
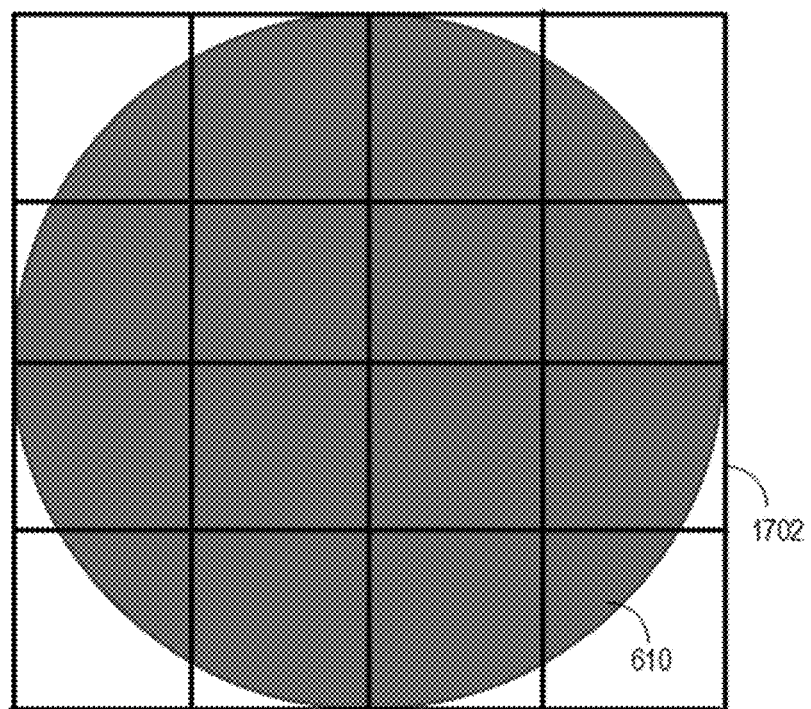

The process may include dividing the microplate, e.g., the microplate 600 of FIGS. 6-7 and 9-10, into four equally-sized quadrants, each quadrant including 24 wells, such as the wells 610 of the microplate 600. For each of the wells, multiple images may be obtained before a complete image of each well is achieved. For example, a top down view of one well 610 is shown in FIG. 17. When preparing to execute imaging of the well 610, the process may include overlaying a grid 1702 with the well 610 to provide an array of regions upon which the objective may be aligned. Images of each section of the grid 1702 may be captured and compiled to provide a complete image of the well 610.

While a focus of a corresponding objective on each section of the grid 1702 may be adjusted by the stage, e.g., the stage 1150 of FIGS. 11A, 11B, 13 and 14, the focus of the objective along the depth of the well 610, e.g., along the z-axis, may be modified by varying a height of the objective. For example, a distance along the z-axis between the objective and the microplate may be modulated by adjusting the vertical position of the objective, e.g., by an automated or manual mechanism as described above. The vertical adjusting of the objective may be conducted to align the focus of the objective with a target interface of the microplate.

Figure 18:
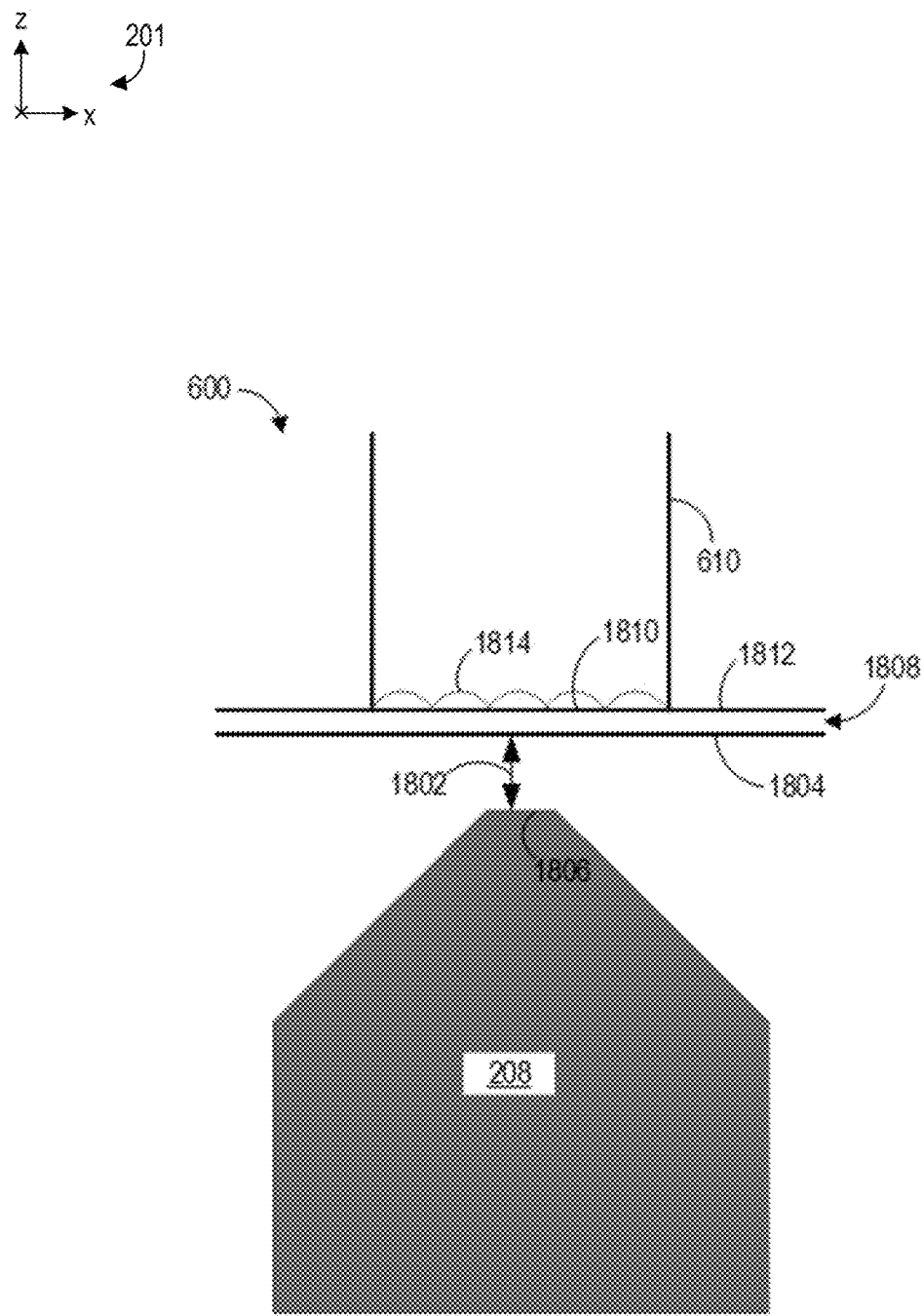
FIG. 18 shows a schematic diagram of the objective position under a well of the microplate.

Interfaces present in the microplate 600 are depicted in a diagram shown in FIG. 18 illustrating a side view of the well 610 and the objective 208 positioned below the well 610. As the well 610 (and the microplate in which the well 610 is disposed) is held stationary with respect to the z-axis, a distance 1802 between a bottom surface 1804 and a tip 1806 of the objective 208 may be varied by modifying the vertical position of the objective 208. Adjustment of the vertical position of the objective 208 may accommodate variations in a target interface for obtaining images across the microplate 600.

The well 610 includes a base 1808 forming a floor of the well 610, where the bottom surface 1804 of the well 610 is also the first interface 1804 of the base 1808. The first interface 1804 may be an interface between the base 1808 and air, e.g., air external to and surrounding the objective 208. The base 1808 also includes a second interface 1810, the second interface 1810 positioned above the first interface 1804. The second interface 1810 may be an interface between an upper surface 1812 of the base 1808 and a sample 1814 placed in the well 610. The sample 1814 may be, in one example, a biological specimen configured to fluoresce in response to illumination by incident light.

The base 1808 may be formed of a transparent material, such as plastic or glass, that does not interfere with light transmission. A target focal depth of the objective 208 may be located at the second interface 1810 to obtain images of the sample 1814 with minimal distortion and interference from reflected light. Focusing of the objective 208 at the second interface 1810 may rely on the LAF, e.g., the LAF sensor 342 of FIGS. 3-4, of each quantitative microscopy assembly of the multi-detector assembly and algorithms, hereafter, autofocus algorithms, for adjusting the vertical position of the objective 208, the algorithms stored at a memory of the controller and executed by the controller when images of the microplate are to be collected.

In contrast to conventional alignment of the objective 208, where alignment of the objective 208 refers to adjustment of the vertical position of the objective 208 to align the focus of the objective 208 at the target interface, the objective 208 may be aligned mechanically. By mechanically aligning the objective, a more robust method for separating LAF reflection signals from sample signals is enabled. For example, the laser beam generated by the LAF sensor may be at least partially reflected at the first interface 1804 and focusing of the objective 208 on the second interface 1810 may only occur upon identification of which signals received by the detector, e.g., the camera 338 of FIGS. 3-4, are undesirable signals generated by reflection at the first interface 1804 and which signals are target signals reflected by the second interface 1810.

A faster and more reliable process for focusing the objective on the second interface 1810 may be provided in combination with the autofocus algorithms. The autofocus algorithms allows the target focal plane to be found and to be utilized to align the focus of the objective 208, based on a laser light shape which may be viewed at an entry aperture of the objective 208. In one example, autofocusing of the objectives may rely on triangulation with oblique illumination. For example, a first, conventional light shape 1900 is shown in FIG. 19 for comparison with a second light shape 2000 shown in FIG. 20. The second light shape 2000 may be used in the multi-detector system 200 to align the focus of each of the objectives. The light shapes may be produced by passing the laser beam of the LAF sensor to an aperture stop or one or more half-moon masks, which may bisect the beam. In one example, the bisected beam may form an image of a half-circle when reflected from the microplate.

Turning first to FIG. 19, the first light shape 1900 includes an objective entry aperture 1902 overlaid with a first LAF beam 1904, the LAF beam 1904 represented as a shaded half-circle. A sharp edge 1906 of the first LAF beam 1904 is aligned with a center of the objective entry aperture 1902. The first LAF beam 1904 therefore overlaps with half of an area of the objective entry aperture 1902 when the objective focus is aligned with a target focal plane. As an example, the user may predefine an offset between a reference plane at the target focal plane. A pair of offset adjustment lenses may be used to maintain the objective focus at the offset from the target focal plane. When the objective focus is out of focus, e.g., not aligned with the target focal plane at the microplate, the first light shape 1900 may be altered. For example, a shape, size, or alignment of the first light shape 1900 may change, thereby demanding vertical adjustment of the objective position.

In some examples, a refractive index of the base of the microplate well may not enable differentiation between reflections from an interface of the base corresponding to the target focal plane (e.g., the second interface 1810 of FIG. 18) from another interface of the base, (e.g., the first interface 1804 of FIG. 18). To address this issue, a modified light shape may be used instead for autofocusing the objectives of the multi-detector system 200.

For example, turning to the second light shape 2000 of FIG. 20, the objective entry aperture 1902 may also be overlaid with a second LAF beam 2002. The second LAF beam 2002 has a smaller area than the first LAF beam 1904 and a sharp edge 2004 of the second LAF beam 2002 is not aligned with the center of the objective entry aperture 1902. Instead, the second LAF beam 2002 overlaps with less than half of the objective entry aperture 1902. In one example, the second LAF beam 2002 may overlap with one fifth of the area of the objective entry aperture 1902. As described above, the second light shape 2000 of FIG. 20 may provide increased separation between light reflected from the first interface 1804 and light from the second interface 1810 of FIG. 18.

For example, a smaller light shape area may increase a separation between reflected laser light sports from each interface of the microplate well base. A first reflection of the laser beam represents reflection from the first interface 1804 and a second reflection represents reflection from the second interface 1810. The increased separation between the first and second reflections arising from use of the smaller light shape results in a greater range through which the objective may be out of focus and still successfully be autofocused on a target interface, e.g., the second interface 1810.

The enhanced ability to identify reflected light resulting from the mechanical alignment depicted in FIG. 20 enables high speed focusing of the objective on the second interface 1810 of FIG. 18. The autofocus algorithms may include setting two autofocus ranges: a first range configured to reach an air/base interface, such as the first interface 1804 of FIG. 18, and a second range configured to reach a base/sample interface, such as the second interface 1810 of FIG. 18, where the base refers to a base of a microplate well, such as the base 1808 of FIG. 18. The second range may be set at a farther distance from the objective than the first range, e.g., the second range is above the first range, and may be selected as a target range which includes the target focal plane of the objective at the base/sample interface. Image collection may be initiated only when the objective focus is adjusted to target focal plane within the second range which may be determined based on the laser beam emitted by a laser source of the LAF sensor of each blade of the multi-detector assembly, such as the LAF sensor 342 of FIGS. 3-4. The laser beam is reflected from the microplate and directed to a detector (such as a CCD camera) of the LAF sensor 342 to produce a light shape image, such as the second light shape 2000 of FIG. 20. The light shape image generated by the LAF sensor may be used to triangulate a position of the objective relative to the base of the microplate well.

Figure 21:
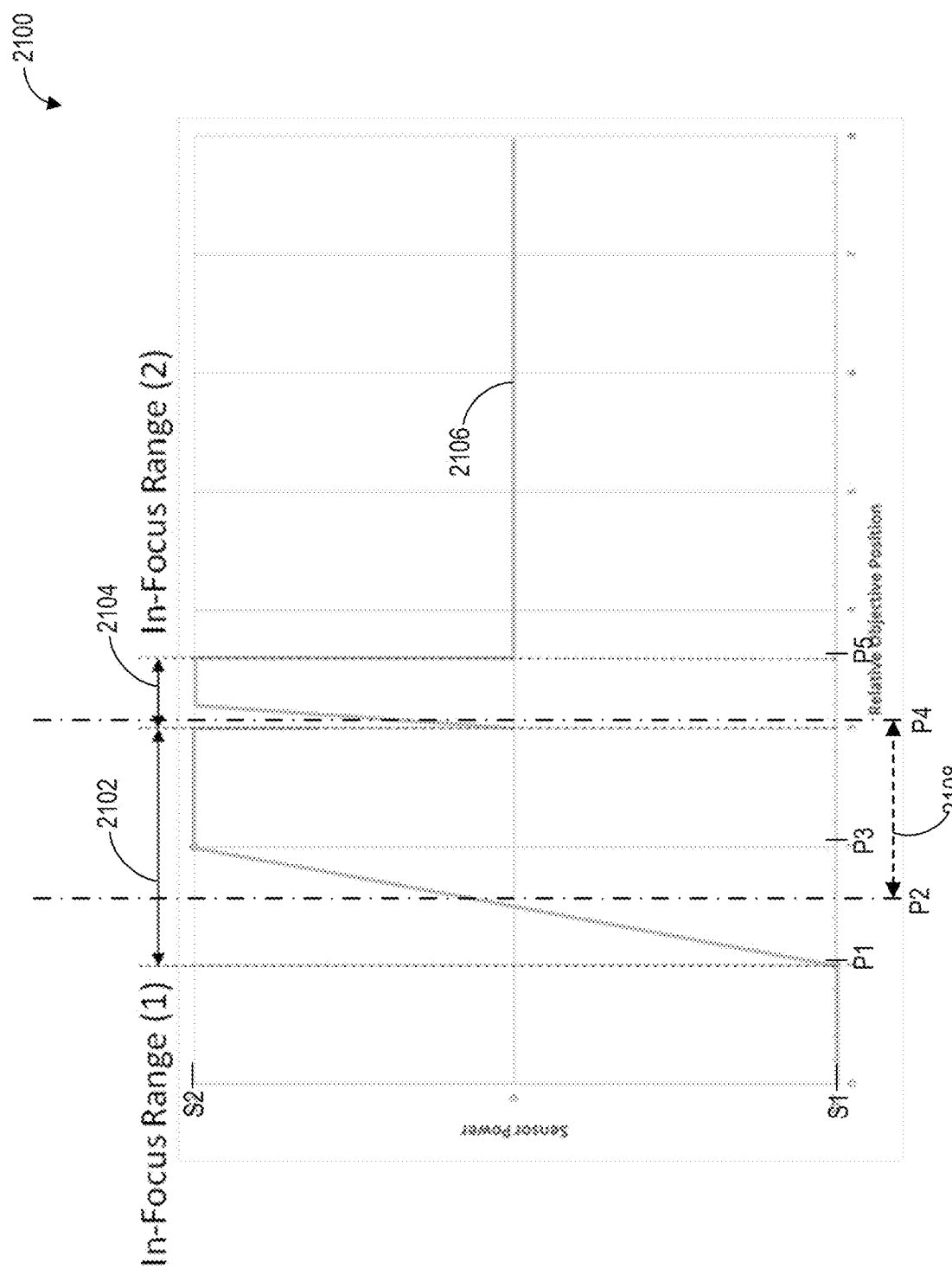
FIG. 21 shows a first plot showing a focusing of a microscope using the light shape of FIG. 19.
Figure 22:
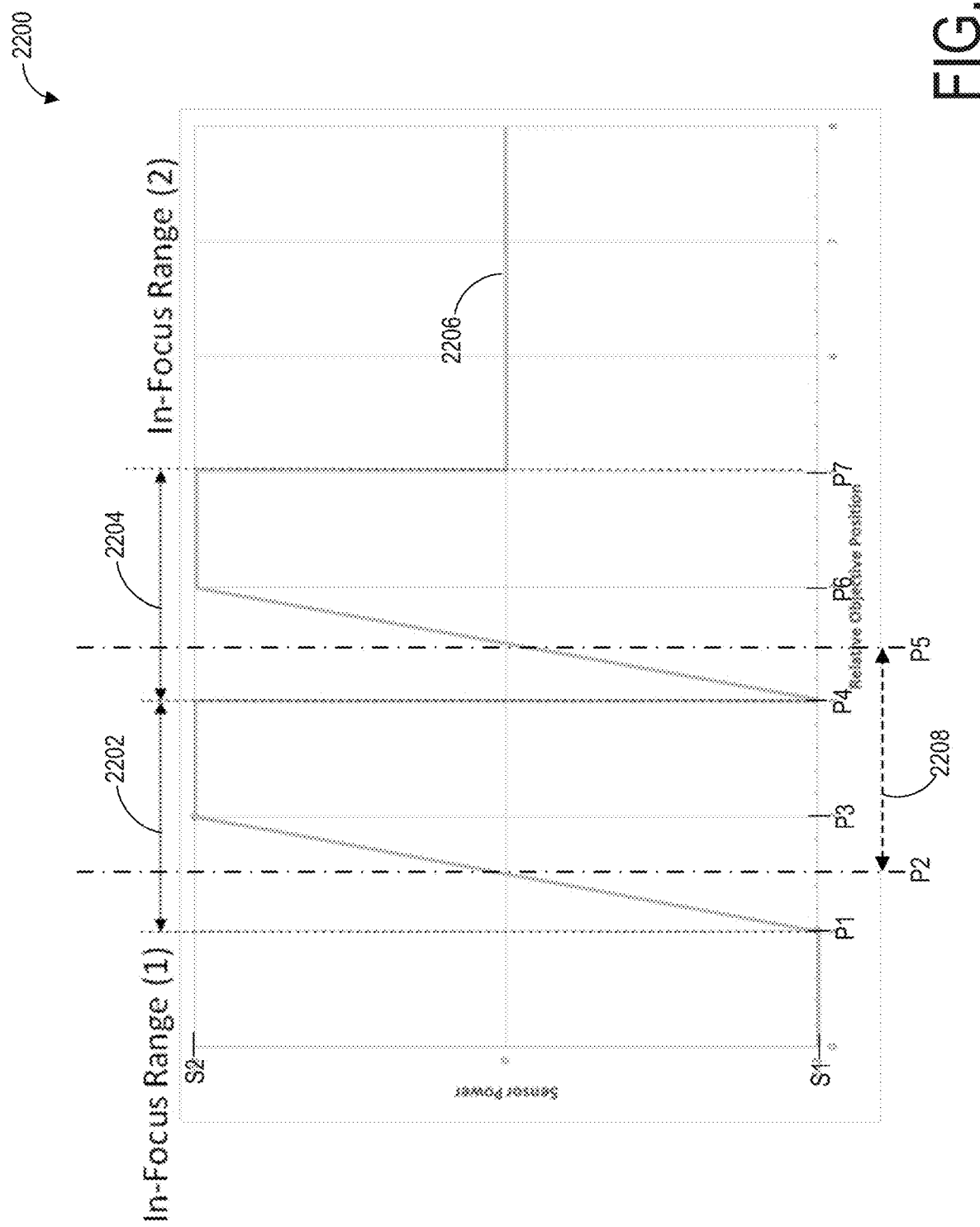
FIG. 22 shows a second plot showing a focusing of an objective of the multi-detector quantitative microscopy system using the light shape of FIG. 20.

For example, variations in a sensor readout of the LAF sensor corresponding to relative objective position is plotted in a first graph 2100 and a second graph 2200 in FIGS. 21 and 22, respectively. The sensor readout may be a unit-less value that is correlated with a distance of the objective, e.g., along the z-axis in FIGS. 3-4, from a position where the objective is in-focus. In one example, a minimum value for the sensor readout may be −512 and a maximum value may be +512. The sensor readout value increasing upwards along the y-axis of the first and second graphs 2100, 2200. When the sensor readout value equals zero, the objective is either in-focus or so far out of focus that the sensor is not detecting the reflected laser beam.

Along the abscissa in the first and second graphs 2100, 2200, the relative objective position moves upwards, towards the sample, to the right. The relative objective position may be a position of the objective along an optical axis of the objective, e.g., along the z-axis in FIGS. 3-4, below a sample or sample holder, e.g., a floor of a microplate well. The first graph 2100 may be representative of data collection and processing at the detector of the LAF sensor for the objective focus alignment based on the first light shape 1900 of FIG. 19 (e.g., conventional alignment) and the second graph 2200 may be representative of data collection and processing of the objective focus alignment based on the second light shape 2000 of FIG. 20.

As shown in the first graph 2100 of FIG. 21, the first range (e.g., of the air/base interface) is indicated along the abscissa by arrow 2102 and the second range (e.g., of the base/sample interface) is indicated by arrow 2104. A first plot 2106 of the first graph 2100 depicts a change in sensor readout value according to the relative objective position through each of the first range 2102 and the second range 2104. For example, at a first point, P1, the objective is at a greatest allowable distance away from the sample and the sensor readout value is at the minimum.

Between a point P1 along the abscissa and a second point P2, the objective may be below the air/base interface and the sensor readout values are negative. The objective focus is aligned with the air/base interface when the sensor readout value is equal to zero at the second point P2. Between the second point P2 and a third point P3 along the abscissa, the objective focus moves above the air/base interface but remains below the base/sample interface, causing the sensor readout value to increase to the maximum value at the third point P3 and plateau at S2 between the third point P3 and a fourth point P4. At the plateau, the sensor may detect that the objective is approaching a surface but cannot determine how close the objective is to the surface.

At a fourth point P4 along the abscissa, the objective focus becomes aligned with the base/sample interface and the sensor readout value drops abruptly to zero. Between the fourth point P4 and a fifth point P5, the objective focus moves above the base/sample interface and the sensor readout value remains at the maximum until the objective position reaches the fifth point P5, which may be an end point of the second range. The sensor power drops to zero power at the fifth point P5 due to the objective moving out of focus. A distance between P2 and P4, with respect to the relative objective position, is indicated by arrow 2108.

As described above, the sensor readout value may be at zero either when the objective focus is aligned with one of the interfaces or when the objective is out of focus, e.g., outside of each of the first range and the second range. The sensor may be configured to distinguish between alignment with an interface and being out of focus by monitoring a change in the sensor readout value when the objective is shifted up or down relative to position when the sensor readout value is zero. For example, if the sensor readout value remains at zero when the objective is moved up or down, the sensor may determine that the objective is out of focus. Alternatively, if the sensor readout value changes in response to moving the objective up or down, the sensor may determine that the objective is in or near a position where the objective is in-focus.

In the second graph 2200 of FIG. 22, the first range is indicated along the abscissa by arrow 2202 and the second range is indicated by arrow 2204. As described above, the objective is within each of the first and the second ranges when sensor readout value is between the minimum value and the maximum value and in-focus within each range when a second plot 2206 of the second graph 2200 crosses zero. At a first point P1 along the abscissa, the objective focus is below the air/base interface and the sensor readout value is at the minimum. The sensor readout value increases between the first point P1 and a second point P2, at which the objective focus is aligned with the air/base interface and the sensor readout value is at zero. Between the second point P2 and a third point P3, the objective focus is above the air/base interface and the sensor readout value increases to the maximum value and plateaus at the maximum value between the third point P3 and a fourth point P4. At the plateau, the sensor may detect that the objective is approaching a surface but cannot determine how close the objective is to the surface. At the fourth point P4, the objective focus reaches a beginning of the second range, below the base/sample interface, and the sensor readout value drops to the minimum value.

When the objective focus is within the second range, as indicated by arrow 2204, the sensor power increases between the fourth point P4 and a fifth point P5 at which the objective focus is aligned with the base/sample interface and the sensor readout value is zero. The sensor power rises to the maximum as the objective focus moves above the base/sample interface between the fifth point P5 and a sixth point P6. Between the sixth point P6 and a seventh point P7, the seventh point P7 defining an end point of the second range, the sensor power plateaus again at the maximum value until dropping to zero power at the seventh point P7. Beyond the seventh point P7, the objective is out of focus. A distance between P2 and P5, with respect to the relative objective position, is indicated by arrow 2208.

Comparison of the first graph 2100 to the second graph 2200 shows that the distance between the alignment of the objective focus with the air/base interface and with the base/sample interface is greater in the second graph 2200 than in the first graph 2100. Thus the objective may move a greater distance in between focusing on the air/base interface and the base/well interface, enabling the interfaces to be differentiated more robustly.

A method for adjusting the focus of the objective to align with the base/sample interface (e.g., the second interface 1810 of FIG. 18) is depicted in a view of relative objective position in FIG. 23 and a block diagram in FIG. 24 and will be described in conjunction with one another. The method may be stored in a memory of the controller (e.g., the controller 124 of FIG. 1), included in the autofocus algorithms, as well as instructions for carrying out the method by the controller. The controller may execute the method based on the LAF sensor of each blade of the multi-detector assembly and/or based on commands input by an operator.

Figure 23:
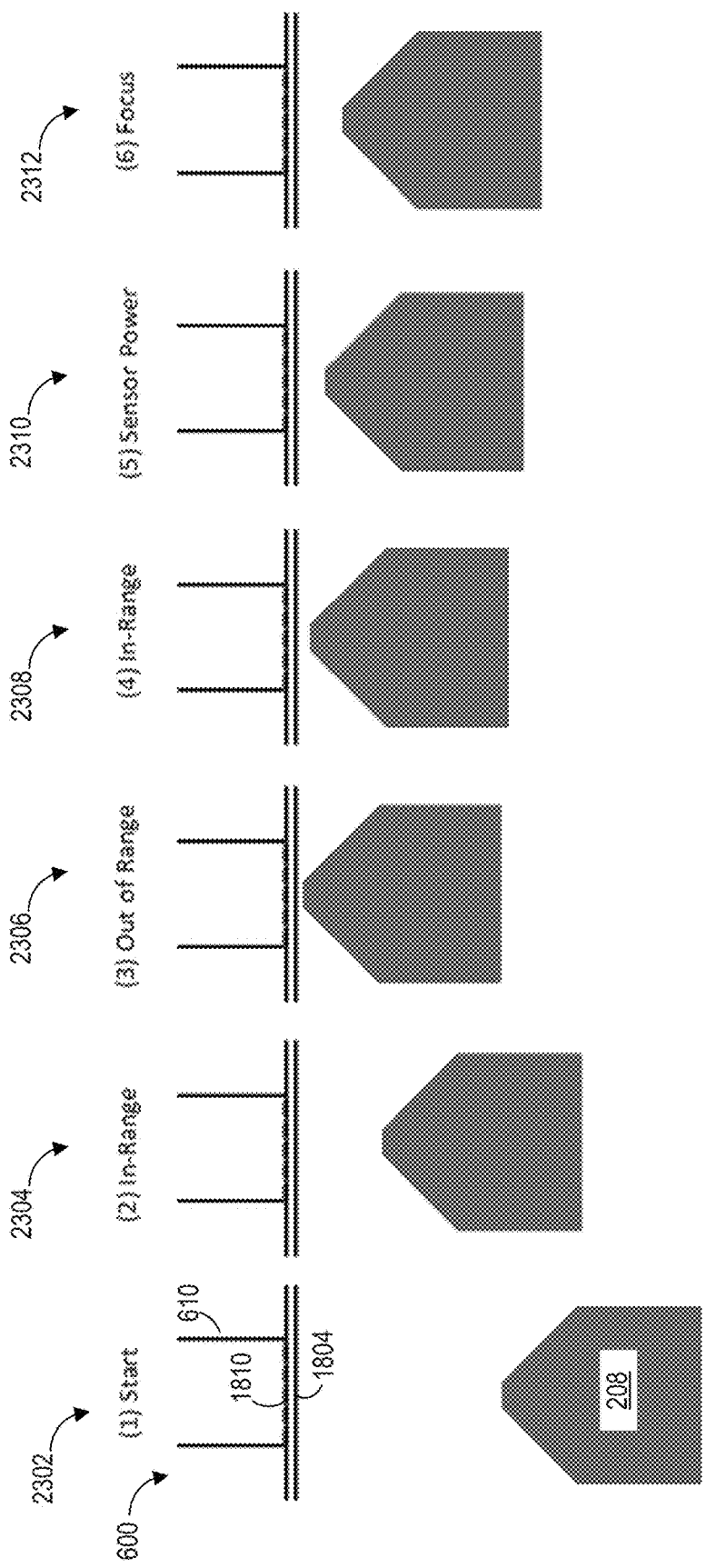
FIG. 23 shows a diagram illustrating a positioning of an objective during an autofocusing method of the multi-detector quantitative microscopy system.

As shown in FIG. 23, the objective 208 is positioned at varying distances below the well 610 of the microplate 600 according to each step of the method. The method may begin with the objective at a nominal position, as shown at a first step 2302 of FIG. 23. The nominal position may be, for example, a resting position that the objective returns to when the multi-detector system is turned off, when the microplate 600 is removed or replaced, and/or when image acquisition is complete. At the resting position, the objective may be positioned at a lowest possible point relative to the height of the blade and a further distance away from the microplate. The first step 2302 corresponds to 2402 of FIG. 24, at which the method includes confirming and/or adjusting the objective to the nominal position while positioned below the well 610 of the microplate 600.

Figure 24:
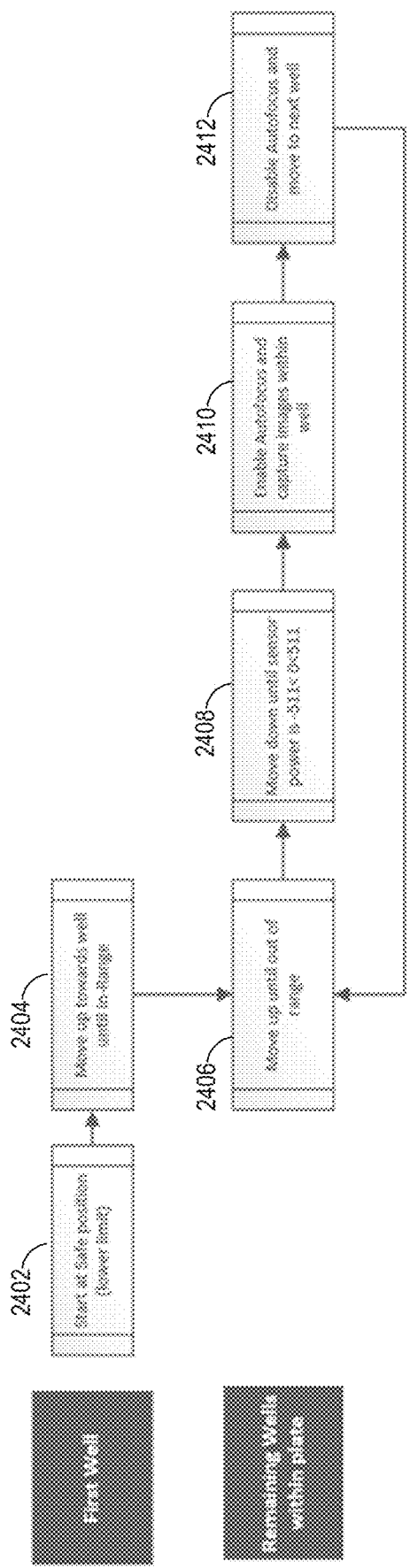
FIG. 24 shows a flow diagram of the autofocusing method of FIG. 23.
Figure 25A:
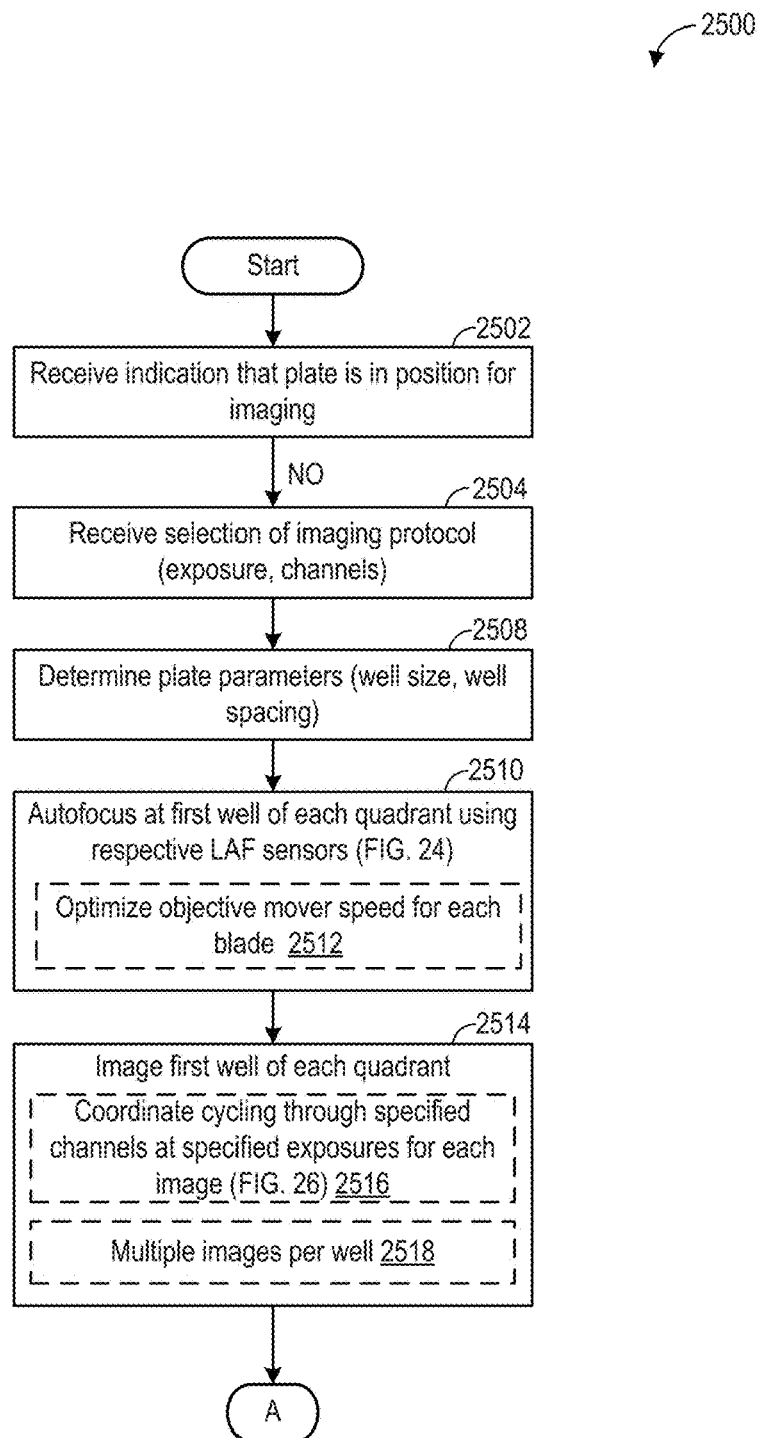
FIGS. 25A-25B show an example of a method for collecting images of the microplate by via the multi-detector quantitative microscopy system.
Figure 25B:
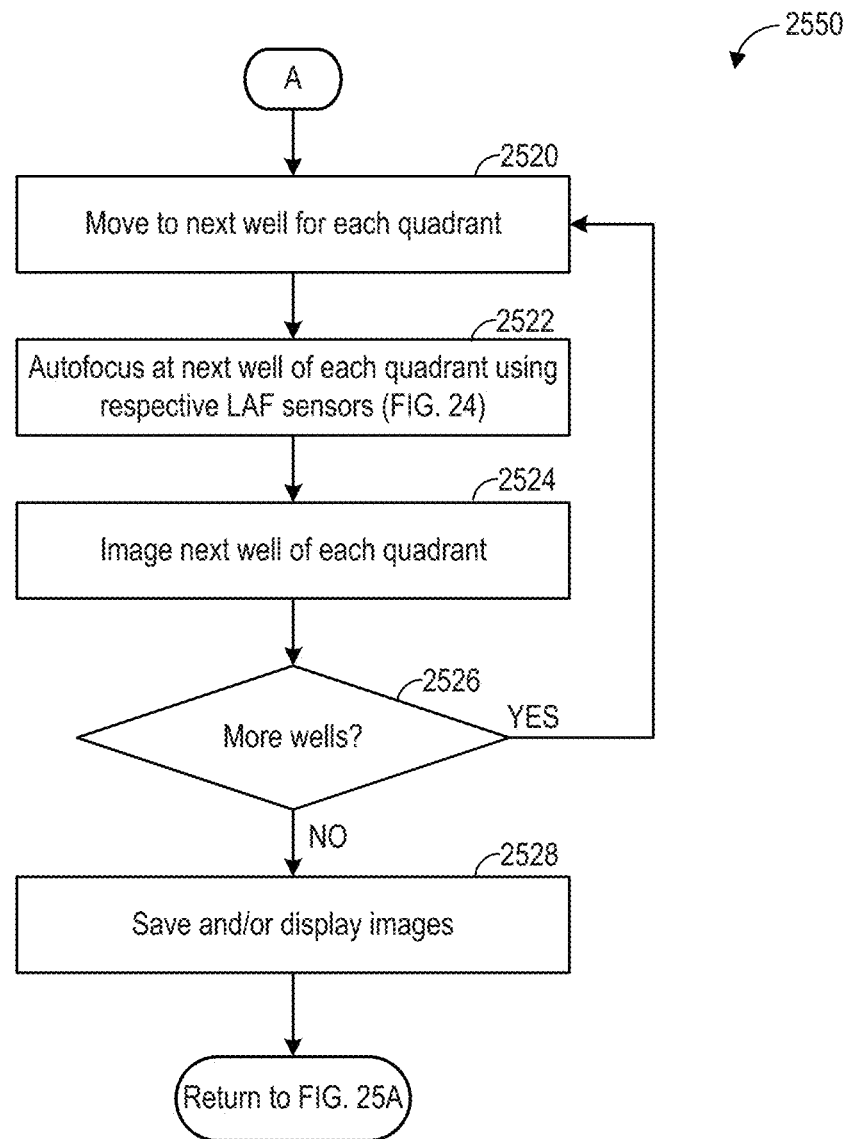

At step 2304 of FIGS. 23 and 2404 of FIG. 24, the method includes raising the vertical position of the objective 208 until the focus of the objective is within the second range of indicated by arrow 2204 in FIG. 22 of the second interface 1810, the second interface 1810 indicated in FIG. 23. For example, the objective may be raised to the relative objective position corresponding to a left-most point of the second range indicated by arrow 2204 of FIG. 22. Upon determining that the objective 208 is in the second range, the vertical position of the objective 208 is further raised at 2406 of FIG. 24, and shown at step 2306 in FIG. 23, until the objective 208 is beyond the second range, e.g., past the right-most point of the second range indicated by arrow 2204 of FIG. 22. The distance between the objective 208 and the microplate 600 may be minimized.

The objective 208 is lowered at 2408 of FIG. 24, also shown at step 2308 of FIG. 23, until the sensor power is within a target low power and a target high power. For example, as shown in FIG. 22, the objective 208 may be lowered to a point within the second range (as indicated by arrow 2204) where the sensor power is between S1 and S2. At step 2310 of FIG. 23, the objective 208 is lowered until the sensor power is at zero. At 2410 of FIG. 24, the method includes using the LAF sensor to make fine adjustments to the vertical position of the objective 208 until the second interface 1810 is in-focus. As shown at step 2312 in FIG. 23, the objective 208, in one example, may be lowered further to maximize a resolution and FOV of the objective 208. Images of the well 610 may be captured until sufficient data is collected. For example, the well 610 may be overlaid with the grid 1702 of FIG. 17, thereby demanding collection of 16 images to generate a complete image of the well 610 while adjusting a horizontal position of the microplate 600 (e.g., along the x-y plane) via the stage 1150 of FIGS. 11A, 11B, and 14.

At 2412 of the method, as shown in FIG. 24, the LAF sensor is disabled, e.g., deactivated, and the horizontal position of the microplate 600 is adjusted to align the objective 208 with a different well of the microplate 600. With each new well, 2406 to 2412 of FIG. 24 and steps 2306 to 2312 of FIG. 23 may be repeated. As such, a time for re-focusing the objective when transitioned to a new well of the microplate for image collection may be reduced while an accuracy of the LAF system, with respect to selecting the correct interface, is increased. Furthermore, each objective of the multi-detector assembly may capture images concurrently. The method described above with reference to FIGS. 23 and 24, based on the second light shape 2000 of FIG. 20, may be implemented at each quantitative microscopy assembly at the same time, allowing parallel screening of each quadrant of the microplate.

In this way, a focus of each objective of the multi-detector system may be rapidly aligned with the base/sample interface of a microplate well. The fast autofocusing of the objectives allows image collection and processing to be expedited, thereby enhancing an efficiency of the multi-detector system. By utilizing a laser light shape with a reduced area, a separation between a focus range of the air/base interface and the base/sample interface may be increased, allowing more efficient focusing of the objective with the target interface (e.g., the base/sample interface) using the autofocus system.

Autofocusing of the multi-detector system, e.g., the multi-detector system 200 of FIGS. 2 and 12-14, may occur independently at each blade of the multi-detector system. However, generation of complete, cohesive images of a microplate may depend on synchronization of image data collected concurrently at each quantitative microscopy assembly of the multi-detector system. A method 2500 for synchronizing imaging data from each detector of the multi-detector system is shown in FIGS. 25A-25B. Instructions for carrying method 2500 may be executed by a controller, such as the controller 124 of FIG. 1, based on instruction stored on a memory of the controller and in conjunction with signals received from sensors of the multi-detector system, such as the sensors described above. The controller may employ actuators of the multi-detector system to adjust operation of the system, according to the methods described below.

Turning first to FIG. 25A, at 2502, method 2500 includes receiving an indication that the microplate is adjusted to a position suitable for imaging. The indication may include, for example, confirmation that the microplate is inserted into a plate holder of the multi-detector system, such as the plate holder 700 of FIGS. 7-11B, and 13-14. The plate holder may include, as an example, a position sensor monitoring a position of a ram, such as the ram 1104 of FIGS. 11A-11B, configured to moderate a position of a swing arm of the plate holder. Adjustment of the ram to a retracted position may indicate that the microplate is in place.

As another example, the indication that the microplate is ready for imaging may include receiving confirmation via a LAF sensor at each blade of the multi-detector system, such as the LAF sensor 342 of FIGS. 3-4. For example, the LAF sensor may emit a laser beam to be reflected from a surface of the microplate, such as a surface at a base of a microplate well supporting a sample. If any of the sensors does not receive a suitable power profile, it is determined that the microplate well is not present or the sample is not present at the microplate well and the microplate may be adjusted to align the objective with the next well. If the suitable power profile is detected by the LAF sensor, a presence of the microplate may be confirmed and image collection may proceed. In some examples, if a stage of the plate holder is shifted through expected dimensions of the microplate and no suitable power profile is detected, an absence of the microplate may be confirmed and the system may be place in a stand-by or shut-down mode.

At 2504, method 2500 includes receiving instructions from a user regarding selection of imaging protocols. For example, an exposure time of each detector of the multi-detector assembly may be input at a graphical user interface (GUI) of the multi-detector system controller. A desired set of channels, where each channel is a target frequency or wavelength of light, for illuminating the microplate may be indicated by the operator at the GUI.

Furthermore, the imaging protocol selection may include indicating how many of the quantitative microscope assemblies of each blade of the multi-detector system are activated to capture imaging data. In some examples, all four blades may be used for image collection. In other examples, less than four of the blades may be used to capture images from select quadrants of the microplate. For example, activation of which quantitative microscope assemblies of the blades may be selected based on a distribution of samples across the microplate.

In some examples, the multi-detector system may be configured or optimized to collect different types of quantitative images. For example, one or more of the detectors may be assigned to fluorescence imaging while one or more of the detectors may be assigned to a different type of assay, or a different combination of fluorescent colors. The detectors may include different filters, light sources, optical benefits, etc. The microplate may therefore be processed by different techniques simultaneously, thereby increasing a flexibility of the multi-detector system for data collection. During instances where speed is prioritized, the detectors may be configured identically.

At 2508, method 2500 includes determining parameters of the microplate. For example, the operator may enter a type of microplate at the GUI, e.g., a 96-well microplate, a 12-well microplate, a 384-well microplate, etc. The controller may refer to a look-up table stored in memory providing physical parameters of each type of plate. As an example, the look-up table may include a well volume, well diameter, a spacing between wells, plate dimensions, etc., specific to the type of microplate. The parameters stored in the look-up table may determine a distance that the microplate is translated, e.g., along the x-y plane, to transition the objective focus between wells to be imaged. The distance may vary according to the microplate type. For example, the microplate may be translated a greater distance from a central focal point of a first well to a central focal point of a second, adjacent well of a 12-well microplate than a 96-well microplate. However, by referring to the look-up table based on identification of the microplate, a speed of transition between wells during imaging may be similar regardless of microplate type.

The method includes, at 2510, auto-focusing each objective of the selected blades at a first well of the corresponding quadrant of the microplate. Auto-focusing of the objectives is enabled via respective LAF sensors included in each blade of the multi-detector system. For example, the method depicted in FIG. 24 for adjusting the objective focus to align with a base/sample interface of the first well may be executed by a LAF controller, the LAF controller communicatively linked to the system controller.

Autofocusing at each objective may also include, at 2512, optimizing a speed at which positions of the objectives, e.g., along the z-axis, are adjusted according to a target positioned determined by the LAF controller. For example, variations in thickness amongst floors of each well of the microplate may result in variations in the target position for each objective. The speed of objective repositioning, e.g., as facilitated by motors in objective modules such as the objective module 328 of FIG. 3, may be selected for each objective based on a desired amount of time for the objectives to be adjusted to the target positions. As an example, a motor of a first objective of the objectives that is furthest displaced from it respective target position may be commanded to operate at a fastest allowable speed to place the objective in the target position rapidly. The speed of the motors of the remaining objectives may be selected based on the motor speed of the first objective such that the remaining objectives are positioned in their respective target positions no later than the first objective.

At 2514, method 2500 includes capturing image data at the first well of each quadrant corresponding to the objectives of the selected blades. Capturing image data may also include, at 2516, coordinating cycling through the specified, e.g., selected, channels at the specified exposures for each collected image, e.g., based on the selection received at 2504. For example, an image at each target focal point may be obtained for each specified exposure. A period of time for capturing a complete suite of images may therefore vary depending on a number of channels and a number of different exposures selected. Further details of coordinating cycling through the specific channels are depicted at FIG. 26.

Figure 26:
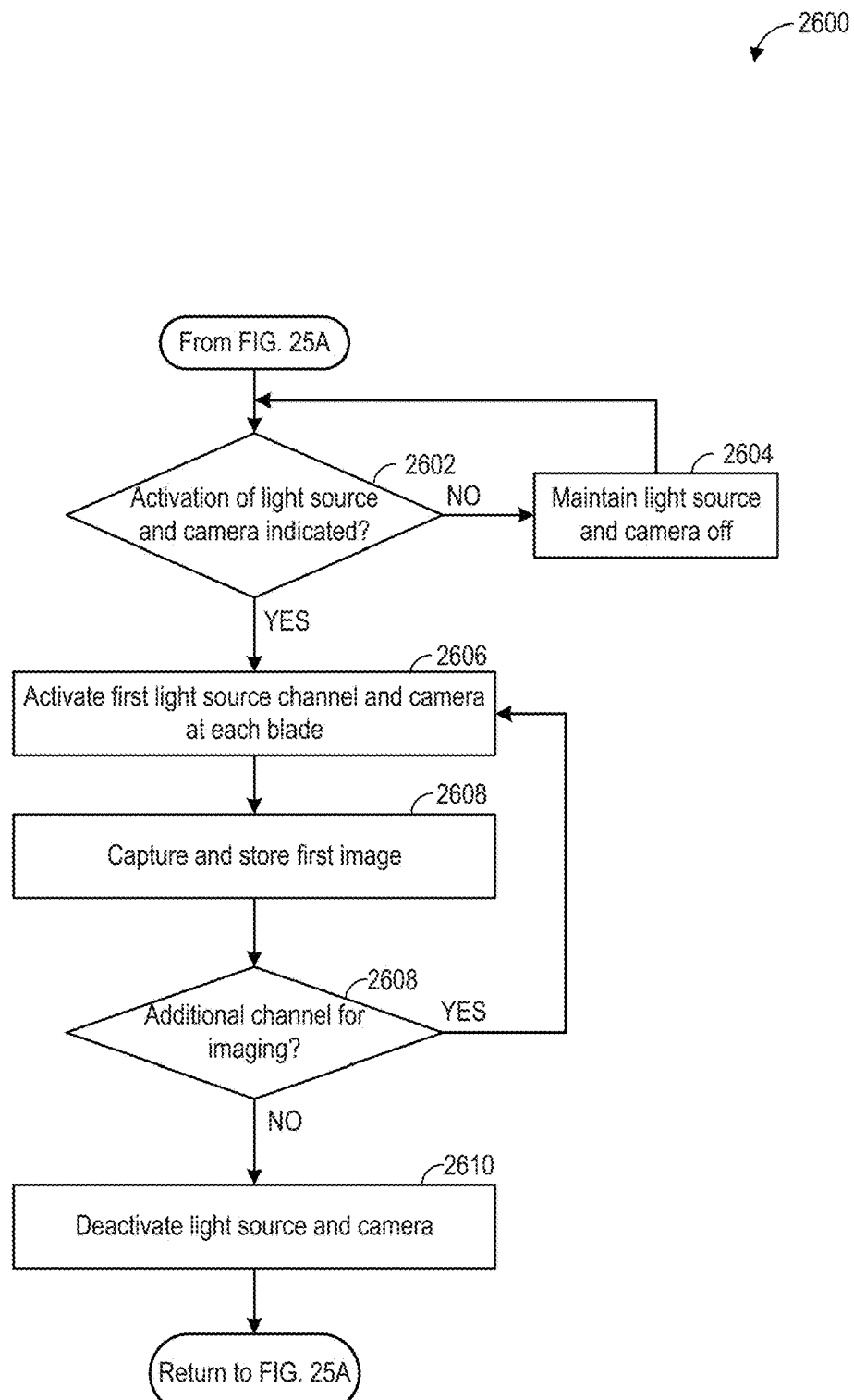
FIG. 26 shows an example of a method for coordination illumination of the microplate by light sources of the multi-detector quantitative microscopy system, which may be executed in conjunction with the method of FIGS. 25A-25B.

Turning now to FIG. 26, a method 2600 for capturing image data at each objective of the multi-detector system is shown. At 2602, method 2600 includes confirming if activation of the light source and the camera are indicated. Activation of the light source and camera may be triggered when the objective of each selected blade is adjusted to the target position to align the objective focus with the target focal plane, as described above with reference to 2510 of method 2500. When each objective is at its respective target position, as determined based on a position sensor of the objective module at each blade, the controller may command activation of the light source and the camera of each blade.

If activation of the light source and the camera is not indicated, method 2600 continues to 2604 to maintain the light source and the camera off, e.g., deactivated. As an example, one or more of the objectives may not be at the target position and additional adjustment to focus the objectives may be demanded. The method returns to 2602 to confirm whether activation of the light source and the camera is indicated.

If activation of the light source and the camera is confirmed at 2602, method 2600 includes activating a first channel at the light source of each selected blade at 2606. In other words, a same LED at each light source is activated to emit a same frequency of light to illuminate the microplate in unison. For example, the first LED 412a of FIG. 4 may be activated at each light source of the selected blades. By emitting light from the same first channel at each of the blades synchronously, a likelihood of signal crosstalk is reduced.

At 2608, method 2600 includes capturing an image at each camera of the selected blades and storing the captured images. For example, the captured images may be stored at the controller's memory, e.g., at a hard drive, to retrieved for further processing and display. Method 2600 includes confirming if another channel of the light sources is to be activated for collecting further image data, according to the received selection of channels at 2504 of method 2500. If another channel is to be activated, method 2600 returns 2606 to activate another channel at the light sources of the selected blades. If no additional channels are to be activated, method 2600 includes deactivating the light sources and the cameras at 2610 and method 2600 returns to method 2500 of FIG. 25A, e.g., at 2514 of method 2500. In instances where more than one exposure is selected for each channel, method 2600 may repeat for each selected exposure before returning to method 2500.

Returning to method 2500, capturing image data at the first well of each quadrant may also include collecting more than one image at the first well, and each subsequent well, of the microplate at 2518. For example, to obtain a complete image of the first well, the focus of each objective may be adjusted, e.g., via translation of the microplate by a stage, to various focal points along the base of the well. In one example, an area of the first well may divided into a 16 by 16 grid, as shown in FIG. 17, and the objective may be focused at each section of the grid. By capturing an image of each section of the grid, the grid images may be compiled into a single, cohesive image of the first well and each successively imaged well. Method 2500 continues at method 2550 of FIG. 25B.

Turning now to FIG. 25B, at 2520, method 2550 includes moving the microplate such that the objectives are focused on a next well of the respective quadrant of the microplate. The new well may be a second well adjacent to the first well or a next closest well supporting a sample. At 2522, method 2550 includes adjusting the objective focus of each selected blade at the next well using the respective LAF sensor, as described with reference to FIG. 24. Image data is collected at 2524 for the next well of each quadrant corresponding to the selected blades.

At 2526, method 2550 includes confirming if additional wells of the microplate are to be imaged. If images of one or more wells of the microplate supporting a sample have not been collected or if image capture at each well of each quadrant is not complete, the method returns to 2520 to continue image data collection at a next well of each quadrant. If no additional wells are to be imaged, e.g., all target wells of each quadrant have been imaged, the method proceeds to 2528 to save and/or display the image data. The image data may include four complete images of four of the microplate wells, each image obtained by one of the objectives. For example, the images may be saved to a database stored in the controller's memory and additionally or alternatively saved to a server in a suitable file format. As an example, the images may be saved in a format that includes metadata. Additionally or alternatively, the images may be displayed at the GUI. Method 2550 returns to the start of method 2500.

In this way, screening of samples on a microplate may be achieved rapidly and efficiently by a multi-detector quantitative microscopy system. The multi-detector quantitative microscopy system (e.g., system) may include two or more microscope assemblies arranged in an x-shaped configuration along a base plate of the system. Each assembly may be configured as a blade including a plate supporting a set of imaging components. Objectives may be located at tops of each blade, protruding upwards through an opening in a housing of the system. The objectives may be clustered around a central axis of the system and spaced further apart along one horizontal axis than along a second, perpendicular horizontal axis. Furthermore, the spacing between the objectives may be selected to enable all objectives to collect images simultaneously, within a targeting imaging region of the microplate during each image collection cycle. As a result, a cycling frequency of microplate image collection may be faster than conventional systems, allowing live biology events to be captured. Various components of the microscope assemblies, such as laser autofocus sensors, a positioning of tube lenses with respect to the objectives with respect to a tube lens, an arrangement of light sources, etc., as well as of the overall system, such as a plate holder for supporting the microplate, may be optimized to contribute to the rapid cycling frequency. Furthermore, a packaging of the system allows the system to have a compact footprint, thereby enabling a portability of the system and reducing its demand for space.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A sample holder for a multi-detector quantitative microscopy system, comprising:
   a frame with a central opening, wherein the central opening is centered over a set of objectives of the multi-detector quantitative microscopy system and configured to receive a microplate;
   a pivotable arm positioned adjacent to the central opening and having a whippletree assembly at a first end of the pivotable arm; and
   a movable ram, in contact with a second end of the pivotable arm, the movable ram configured to pivot the pivotable arm, wherein the pivotable arm includes a first portion extending diagonally relative to a side of the microplate and a second portion, continuous with the first portion, extending parallel with the side of the microplate, wherein the first portion includes the first end of the pivotable arm and the second portion includes the second end of the pivotable arm, and wherein the second portion of the pivotable arm further includes a pivot at a mid-point along a length of the second portion, the pivot configured to couple the pivotable arm to the frame of the sample holder and allow the pivotable arm to rotate about the pivot.

2. The sample holder of claim 1, wherein the first portion of the pivotable arm includes the whippletree assembly, and wherein the whippletree assembly includes a pivotable yoke with two arms arranged perpendicular to one another, the two arms extending along perpendicular sides of the microplate.

3. The sample holder of claim 2, wherein each of the two arms has a contact ball protruding towards the perpendicular sides of the microplate.

4. The sample holder of claim 3, wherein, when the pivotable yoke is pivoted to engage with the microplate, each ball of the contact balls is in contact with one of the perpendicular sides of the microplate and the pivotable yoke is concentric with a corner of the microplate where the perpendicular sides intersect.

5. The sample holder of claim 4, wherein each ball of the contact balls contacts the respective side of the microplate simultaneously when the pivotable yoke is pivoted to engage with the microplate.

6. The sample holder of claim 1, wherein the second portion of the pivotable arm further includes a bearing configured to slide along a direction perpendicular to the length of the second portion, and wherein the sliding of the bearing drives rotation of the pivotable arm about the pivot.

7. The sample holder of claim 6, wherein the rotation of the pivotable arm in a first direction causes the first end of the pivotable arm to swing towards the microplate and rotation of the pivotable arm in a second, opposite direction causes the first end of the pivotable arm to swing away from the microplate.

8. An imaging system, comprising:
a plate holder positioned above a set of objectives of the imaging system, the plate holder configured to hold a microplate in place based on engagement of the microplate by a whippletree assembly of the plate holder, wherein the whippletree assembly includes a yoke with two arms arranged perpendicular to one another and each of the two arms having a contact ball along edges of the two arms proximate to the microplate, and wherein each contact ball is configured to exert a pressure against a side of the microplate, proximate to a corner of the microplate, when the whippletree assembly engages with the microplate.

9. The imaging system of claim 8, wherein the whippletree assembly is coupled to a first end of a pivotable arm of the plate holder, and wherein the pivotable arm is coupled to a bearing at a second end of the pivotable arm, opposite of the first end.

10. The imaging system of claim 9, wherein a position of the bearing is adjusted along a first direction perpendicular to a length of the pivotable arm by a ram driven by the motor, and wherein the ram slides along a second direction parallel with the length of the pivotable arm.

11. The imaging system of claim 10, wherein the ram has a ramped surface in contact with the bearing, and wherein sliding of the ram along the second direction causes the ramped surface to slide along the bearing and drive motion of the bearing along the first direction.

12. The imaging system of claim 9, wherein the whippletree assembly and the pivotable arm are positioned above a frame of the plate holder and the ram and the motor are positioned below the frame of the plate holder, and wherein the bearing extends through an opening in the frame of the plate holder.

13. An imaging system, comprising:
a plate holder positioned above a set of objectives of the imaging system, the plate holder configured to hold a microplate in place based on engagement of the microplate by a whippletree assembly of the plate holder, the whippletree assembly coupled to a first end of a pivotable arm of the plate holder and the pivotable arm coupled to a bearing at a second end of the pivotable arm, opposite of the first end, wherein a position of the bearing is adjusted along a first direction perpendicular to a length of the pivotable arm by a ram driven by the motor, and wherein the ram slides along a second direction parallel with the length of the pivotable arm.

14. The imaging system of claim 13, wherein the whippletree assembly and the pivotable arm are positioned above a frame of the plate holder and the ram and the motor are positioned below the frame of the plate holder, and wherein the bearing extends through an opening in the frame of the plate holder.

* * * * *